US009981934B2

(12) United States Patent
Urano et al.

(10) Patent No.: US 9,981,934 B2
(45) Date of Patent: May 29, 2018

(54) ENZYME-SPECIFIC FLUORESCENT COMPOUND CAPABLE OF BEING RETAINED IN CELLS

(71) Applicant: The University of Tokyo, Tokyo (JP)

(72) Inventors: Yasuteru Urano, Tokyo (JP); Mako Kamiya, Tokyo (JP); Tomohiro Doura, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days. days.

(21) Appl. No.: 15/310,641

(22) PCT Filed: May 13, 2015

(86) PCT No.: PCT/JP2015/063789
§ 371 (c)(1),
(2) Date: Nov. 11, 2016

(87) PCT Pub. No.: WO2015/174460
PCT Pub. Date: Nov. 19, 2015

(65) Prior Publication Data
US 2017/0073321 A1    Mar. 16, 2017

(30) Foreign Application Priority Data

May 14, 2014 (JP) .................... 2014-100771

(51) Int. Cl.
*C07D 311/04* (2006.01)
*C07H 17/04* (2006.01)
*C12Q 1/40* (2006.01)

(52) U.S. Cl.
CPC ........... *C07D 311/04* (2013.01); *C07H 17/04* (2013.01); *C12Q 1/40* (2013.01); *G01N 2333/938* (2013.01)

(58) Field of Classification Search
CPC .................................................. C07D 311/04
See application file for complete search history.

(56) References Cited

U.S. PATENT DOCUMENTS

| 5,093,106 A | 3/1992 | Dzbanovsky et al. |
| 2008/0014602 A1 | 1/2008 | Nagano et al. |
| 2009/0317914 A1 | 12/2009 | Nagano et al. |
| 2012/0052518 A1 | 3/2012 | Nagano et al. |
| 2013/0023675 A1 | 1/2013 | Urano et al. |
| 2014/0206992 A1 | 7/2014 | Urano et al. |

FOREIGN PATENT DOCUMENTS

| JP | 01-211531 | 8/1989 |
| JP | 2014065673 | 4/2014 |
| WO | 2005024049 | 3/2005 |
| WO | 2007100061 | 9/2007 |
| WO | 2010095450 | 8/2010 |
| WO | 2011087000 | 7/2011 |
| WO | 2013180181 | 5/2013 |

OTHER PUBLICATIONS

International Search Report and Written Opinion in International Patent Application No. PCT/JP2015/063789.
Mako Kamiya et al., "Keiko Probe no Seimitsu Sekkei ni Motozuku in vivo Jinsoku Keiko Gan Imaging", Experimental Medicine, 2012, vol. 30, No. 7, pp. 1135 to 1144.
Mako Kamiya et al., "Rhodal no Spiro Kanka Heiko ni Motozuku B-Galactosidase Keiko Probe no Kaihatsu", Japanese Society for Photomedicine and Photobiology, 2012, vol. 34 p. 63.
Kamiya Mako, et al., B-Galactosidase Fluorescence Probe with Impoved Cellular Accumulation Based on a Spirocyclized Rhodol Scaffold, Journal of the American Chemical Society, 2011, vol. 133 (33), p. 12960-12963.
Taki Masayasu, et al., A mitochondria-targeted turn-on fluorescent probe based on a rhodol platform for the detection of copper (I), Organic & Biomolecular Chemistry, May 12, 2014, vol. 12(27), p. 4999-5005.
Florence Debacq-Chainiaux, et al., Protocols to Detect senescence-associated beta-galactosidase (SA-Bgal) activity, a biomarker of senescent cells in culture and in vivo, 2009 vol. 4 No. 12, p. 1806.
Sunil K. Chatterjee, et al. "Glycosyltransferase and Glycosidase Activities in Ovarian Cancer Patients" Cancer Research 39, 1943-1951,Jun. 1979.
H. Bruce Bosmann, et al. "Enzyme Activity in Invasive Tumors of Human Breast and Colon", Proc. Nat. Acad. Sci. USA, vol. 71, No. 5, pp. 1833-1837, May 1974.
Goberdhan P. Dimri, et al. "A Biomarker that identifies senescent human cells in culture and in aging skin in vivo", Proc. Natl. Acad. Sci. USA, vol. 92, pp. 9363-9367, Sep. 1995, Cell Biology.

*Primary Examiner* — Noble E Jarrell
*Assistant Examiner* — John S Kenyon
(74) *Attorney, Agent, or Firm* — Leason Ellis LLP

(57) ABSTRACT

Provided is an enzyme-specific fluorescent compound capable of being retained in cells, which can emit fluorescence specifically in a target cell, particularly a cell capable of expressing a reporter enzyme such as β-galactosidase, and can covalently bind to a protein in the cell to exhibit an excellent property of being retained in the cell. The fluorescent compound comprises a compound represented by formula (I') or a salt thereof. In formula (I'), A, X, Y and R1 to R9 are as described in claim 1.

20 Claims, 10 Drawing Sheets

SDS-PAGE (running gel: 10%T, stacking gel: 4%T, 200 V)   2014/2/21 [TD392]

(a) Fluorescence (b) Absorbance (CBB stain)

(a) 4-CH₂F-HMDER-βGal (no washout)

(b) HMDER-βGal (no washout)

(a) 20 μM 4-CH₂F-HMDER-βGal (b) 20 μM HMDER-βGal esg-lacZ 2014/2/20

(a) After fixed by 4% PFA for 25 min, incubated with 100 μM 4-CH₂F-HMDER-βGal for 10 min and made transparent by 80% glycerol excitation: 514 nm, observed: 535-695 nm (HyD2), 40 magnifications, scale bar: 100 μm esg-GFP (control)

(b) After fixed by 4% PFA and made transparent by 80% glycerol

4-CH₂F-HMDER-βGal was injected to a SHIN3-mouse
After 1 h

ENZYME-SPECIFIC FLUORESCENT COMPOUND CAPABLE OF BEING RETAINED IN CELLS

TECHNICAL FIELD

The present invention relates to a novel fluorescent compound which can be retained in a target cell and can act with specificity in the cell, to a method for specifically imaging a target cell in which a specific enzyme is expressed using the compound, to a probe used in the imaging, to a detection kit comprising the probe, to a detection agent, and to a diagnostic drug or kit. More specifically, the present invention more relates to a fluorescent compound for selectively visualizing a cell in which β-galactosidase or another reporter enzyme is expressed and an imaging method which uses the fluorescent compound, and to an imaging probe, a detection agent, and a diagnostic drug or kit.

BACKGROUND ART

Reporter proteins have made an immeasurable contribution to the advancement of life sciences. The most commonly used reporter protein is β-galactosidase. A relationship between aging and expression of β-galactosidase in cells has recently been suggested (see Non-Patent Reference 1), and imaging probes which are enzyme-specific to β-galactosidase are important molecular tools for elucidating mechanisms of cell aging. Furthermore, β-galactosidase activity has been shown to be elevated in certain types of cancer cells (see Non-Patent References 2 and 3), and an imaging probe which is enzyme-specific to β-galactosidase is thought to be usable also as a cancer-cell-selective fluorescence imaging probe.

Conventional methods for imaging enzyme activity using X-Gal as a substrate are widely used (Non-Patent Reference 4), but X-Gal cannot be applied to living cells, and there is therefore a need to develop a probe for imaging enzyme activity which can be applied to living cells. Numerous imaging probes that can be applied to living cells have presently been developed. For example, HMDER-βGal and the like have been developed as β-galactosidase fluorescent probes which can be applied to living cells and living biological tissues, and in which visible light excitation is possible by control of a spiro-ring-forming reaction in the molecule thereof (see Non-Patent Reference 5 and Patent Reference 1). However, in all of these fluorescent probes, the enzyme reaction product leaks from the cells, or cytotoxic ultraviolet light is used as excitation light, and living cells and the like are difficult to clearly image at a single-cell level. Conventional cancer probes also have drawbacks in that immobilization of a section for pathological diagnosis causes the cancer probe to leak out of cells, making the cancer probe unusable for pathological diagnosis.

PRIOR ART REFERENCES

Patent References

Patent Reference 1: International Publication 2005/024049

Non-Patent References

Non-Patent Reference 1: G. P. Dimri et al., Proc. Natl. Acad. Sci. USA, 1995, 92, pp. 9363-9367.
Non-Patent Reference 2: H. B. Bosmann et al., Proc. Natl. Acad. Sci. USA, 1974, 71, pp. 1833-1837
Non-Patent Reference 3: S. K. Chatterjee et al. Cancer Res., 1979, 39, pp. 1943-1951.
Non-Patent Reference 4: F. D.-Chainiaux et al., Nat. Protoc., 2009, 4, pp. 1798-1806.
Non-Patent Reference 5: M. Kamiya et al., J. Am. Chem. Soc. 2011, 133, pp. 12960-12963.

SUMMARY OF THE INVENTION

Problems to be Solved by the Invention

An object of the present invention is to provide a fluorescent compound for emitting fluorescence in enzyme-activity-specific fashion while at the same time being retained in a cell having the enzyme, whereby the cell can be selectively visualized at a single-cell level in an immobilized state or without being immobilized, and to provide a fluorescence imaging probe which uses the fluorescent compound, a detection method which uses the fluorescent probe, and a detection kit or detection agent.

Means Used to Solve the Above-Mentioned Problems

As a result of intensive investigation aimed at solving the abovementioned problems, the inventors synthesized an enzyme substrate having a substituent which changes a fluorescent dye having a xanthene ring as a fluorophore into a quinone methide after reaction with a reporter enzyme, and discovered that by optimizing the structure of the enzyme substrate, a fluorescence imaging probe is obtained which has excellent retention in a cell, and in which fluorescent properties are exhibited only by reaction with a reporter enzyme such as β-galactosidase. The inventors perfected the present invention on the basis of these findings.

Specifically, an aspect of the present invention provides an enzyme-specific retainable fluorescent compound comprising a compound represented by Formula (I) below or a salt thereof.

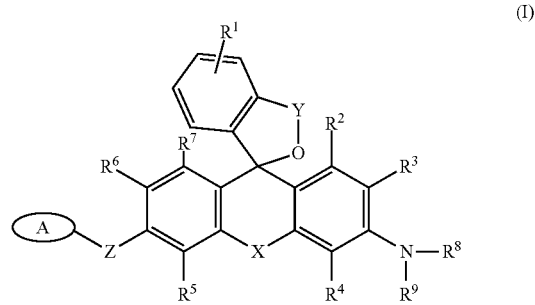

(Wherein, A represents a monovalent group which is cleaved by an enzyme; $R^1$ represents a hydrogen atom or one to four same or different substituents bonded to the benzene ring; $R^3$, $R^4$, $R^5$, and $R^6$ each independently represent —$CFR^{10}R^{11}$ or —$CF_2R^{12}$, or a hydrogen atom, a hydroxyl group, an alkyl group, or a halogen atom; $R^2$ and $R^7$ each independently represent a hydrogen atom, a hydroxyl group, an alkyl group, or a halogen atom; $R^8$ and $R^9$ each independently represent a hydrogen atom or an alkyl group; $R^{10}$, $R^{11}$, and $R^{12}$ each independently represent a hydrogen atom, an alkyl group, or an alkenyl group; X represents an oxygen atom, Se, $CR^{13}R^{14}$, or $SiR^{15}R^{16}$; $R^{13}$, $R^{14}$, $R^{15}$, and $R^{16}$ each independently represent a hydrogen atom or an alkyl group;

Y represents a $C_{1-3}$ alkylene group; Z represents an oxygen atom or $NR^{17}$; $R^{17}$ represents a hydrogen atom or an alkyl group; and at least one of $R^3$, $R^4$, $R^5$, and $R^6$ represents —$CFR^{10}R^{11}$ or —$CF_2R^{12}$.)

In a preferred embodiment, the enzyme-specific retainable fluorescent compound is represented by the formula below.

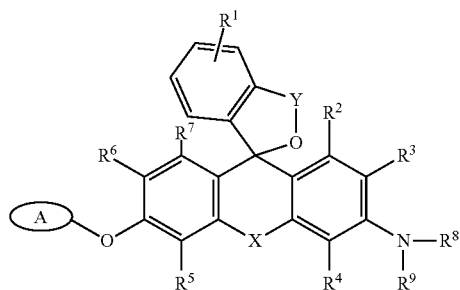
(I')

(Wherein, A, $R^1$ through $R^9$, X, and Y are the same as in Formula (I).)

In a preferred embodiment, at least one of $R^3$, $R^4$, $R^5$, and $R^6$ is —$CFR^{10}R^{11}$.

In a preferred embodiment, at least one of $R^3$, $R^4$, $R^5$, and $R^6$ is —$CH_2F$.

In a preferred embodiment, A is a hydrolase comprising a reporter enzyme, or is a group which is cleaved by an enzyme expressed or activated specifically in a cancer cell. More specifically, A is a galactopyranosyl group, and the reporter enzyme is β-galactosidase.

In a more preferred embodiment, the enzyme-specific retainable fluorescent compound or salt thereof is a compound represented by Formulas (Ia) through (Ic) below or a salt thereof.

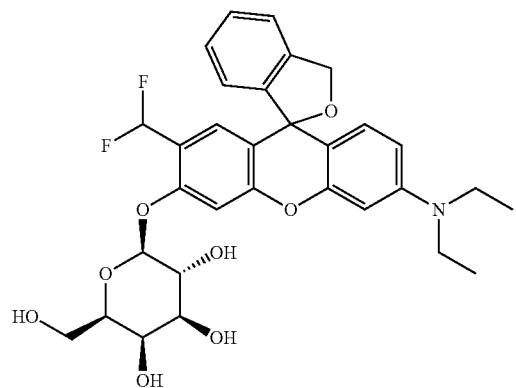
(Ia)

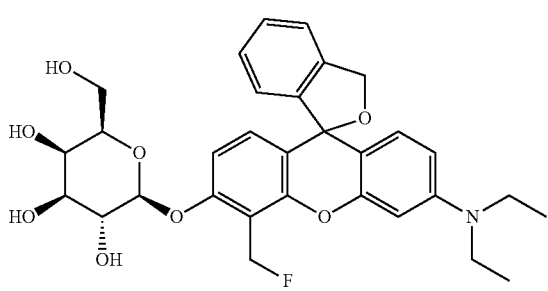
(Ib)

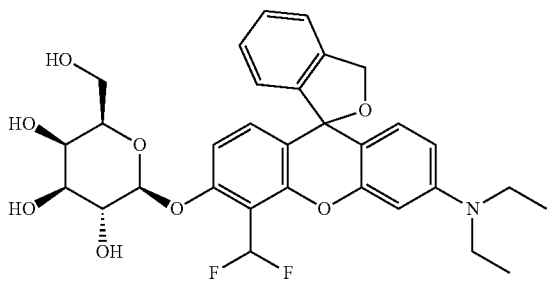
(Ic)

In another aspect, the present invention relates to a fluorescent probe containing the enzyme-specific retainable fluorescent compound represented by Formula (I), (I'), or (Ia) through (Ic).

In another aspect, the present invention relates to a composition or kit for visualizing or detecting a target cell in which a specific enzyme is expressed, the composition or kit containing the enzyme-specific retainable fluorescent compound represented by Formula (I), (I'), or (Ia) through (Ic). Preferably, the target cell is a cell expressing β-galactosidase, and the target cell is more preferably a cancer cell.

In another aspect, the present invention relates to a method for detecting, using the enzyme-specific retainable fluorescent compound represented by Formula (I), (I'), or (Ia) through (Ic), a target cell in which a specific enzyme is expressed. Preferably, in the method, the enzyme-specific retainable fluorescent compound is contacted with an enzyme expressed specifically in a target cell at ex vivo or in vivo, and then the target cell in which a specific enzyme is expressed is detected. More preferably, the present invention relates to a method for detecting a target cell in which the specific enzyme is expressed, the method characterized by comprising a step for bringing the enzyme-specific retainable fluorescent compound into contact with an enzyme expressed specifically in the target cell at ex vivo or in vivo, and a step for performing excitation light irradiation and inducing fluorescence. The target cell in the method is more preferably a cell expressing β-galactosidase, and the target cell is more preferably a cancer cell.

In another aspect, the present invention relates to a compound represented by Formula (II) below, used for manufacturing Formula (I).

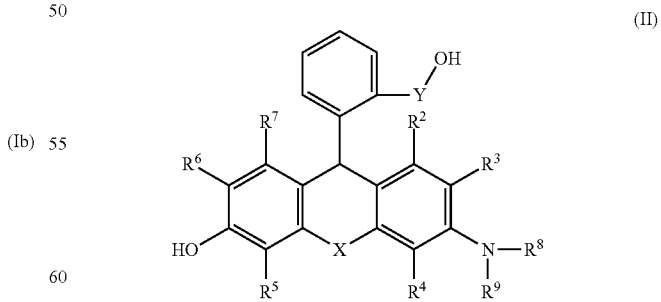
(II)

(Wherein, $R^3$, $R^4$, $R^5$, and $R^6$ each independently represent —C(=O)H, a hydrogen atom, a hydroxyl group, an alkyl group, or a halogen atom; $R^2$ and $R^7$ each independently represent a hydrogen atom, a hydroxyl group, an alkyl group, or a halogen atom; $R^8$ and $R^9$ each independently represent a hydrogen atom or an alkyl group; X represents an oxygen atom or Se, $CR^{13}R^{14}$, or $SiR^{15}R^{16}$; $R^{13}$, $R^{14}$, $R^{15}$, and $R^{16}$ each independently represent a hydrogen atom or an alkyl group; Y represents a $C_{1-3}$ alkylene group; and at least one of $R^3$, $R^4$, $R^5$, and $R^6$ represents —(=O)H.)

In a more preferred embodiment, the compound of Formula (II) is a compound represented by Formula (IIa) or (IIb) below.

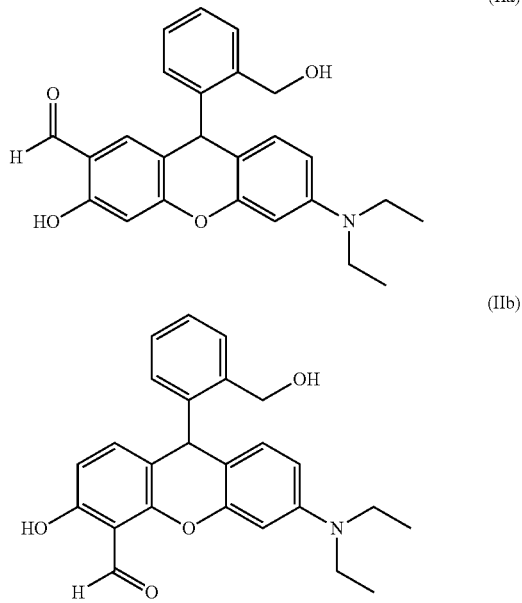

Advantages of the Invention

The enzyme-specific retainable fluorescent compound of the present invention changes visible light absorption by enzyme reaction, and, at the same time, covalently bonds to a protein coexisting in a cell using the generated quinone methide, and thereby exhibits excellent retention in the cell. As a result of the combination of these effects, a target cell expressing the enzyme can be visualized at a single-cell level of detail in the state thereof as a living cell or in an immobilized state. The enzyme-specific retainable fluorescent compound of the present invention can be used as a molecular tool for elucidating mechanisms of cell aging, and may also be usable as a selective fluorescence imaging probe in certain types of cancer cells. Furthermore, an imaging method using the enzyme-specific retainable fluorescent compound of the present invention can be implemented using a normal microscope capable of cell imaging, and does not require a special device. The present invention also enables fluorescence imaging at a single-cell level, and therefore makes it possible to track changes in individual cells over time, and also to surgically excise cancer tissue so as to leave none behind, using cancer-cell-selective fluorescence imaging. The enzyme-specific retainable fluorescent compound of the present invention is thus considered to have extremely significant industrial utility value and economic effect.

HMDER-βGal can be applied in fluorescence imaging of a biological tissue. (a) Image of fly wing primordia tissue reacted with 4-CH₂F-HMDER-βGal, including, from left, a fluorescence image, a bright field image, and a merged image thereof. (b) Image of fly wing primordia tissue reacted with HMDER-βGal, including, from left, a fluorescence image, a bright field image, and a merged image thereof.

Figure 11:
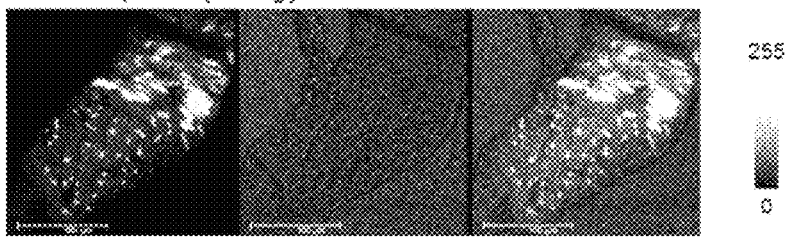
Figure 11:
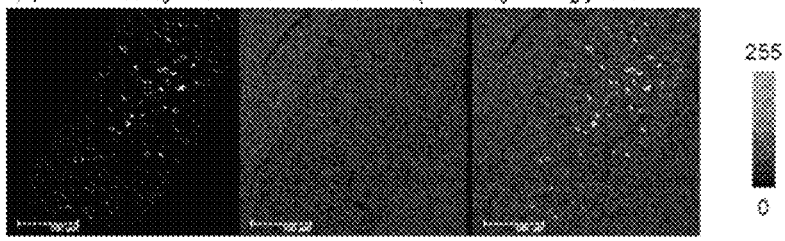

FIG. 11 A view indicating that the enzyme-specific retainable fluorescent compound of the present invention 4-CH₂F-HMDER-βGal can be applied in single-cell fluorescence imaging. (a) Image of a fruit fly (esg-lacZ) reacted with 4-CH₂F-HMDER-βGal, including, from left, a fluorescence image, a bright field image, and a merged image thereof. (b) From left, a fluorescence image, a bright field image, and a merged image thereof for *Drosophila* intestinal stem cells (esg-GFP).

Figure 12:
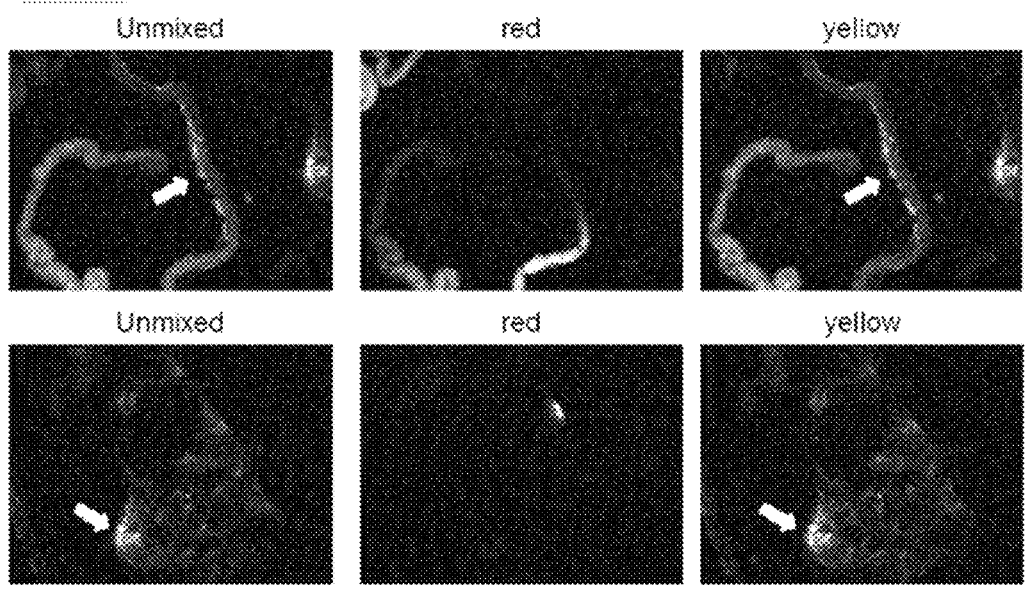

FIG. 12 A fluorescence spectrum image indicating that the enzyme-specific retainable fluorescent compound of the present invention 4-CH₂F-HMDER-βGal can be applied in cancer-site-selective fluorescence imaging. The white arrow indicates the position of a tumor. In the unmixed images, autofluorescence and a fluorescence spectrum are separated by fluorescence spectra.

Figure 13:
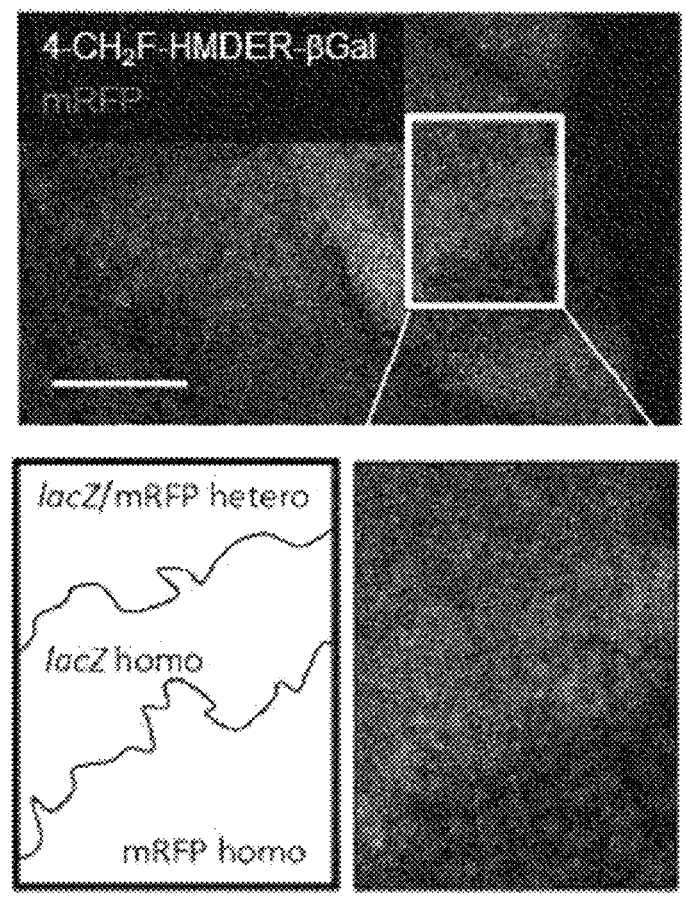

FIG. 13 A view indicating that the enzyme-specific retainable fluorescent compound of the present invention 4-CH₂F-HMDER-βGal can be applied in fluorescence imaging of a non-immobilized cell group in vivo.

Figure 14:
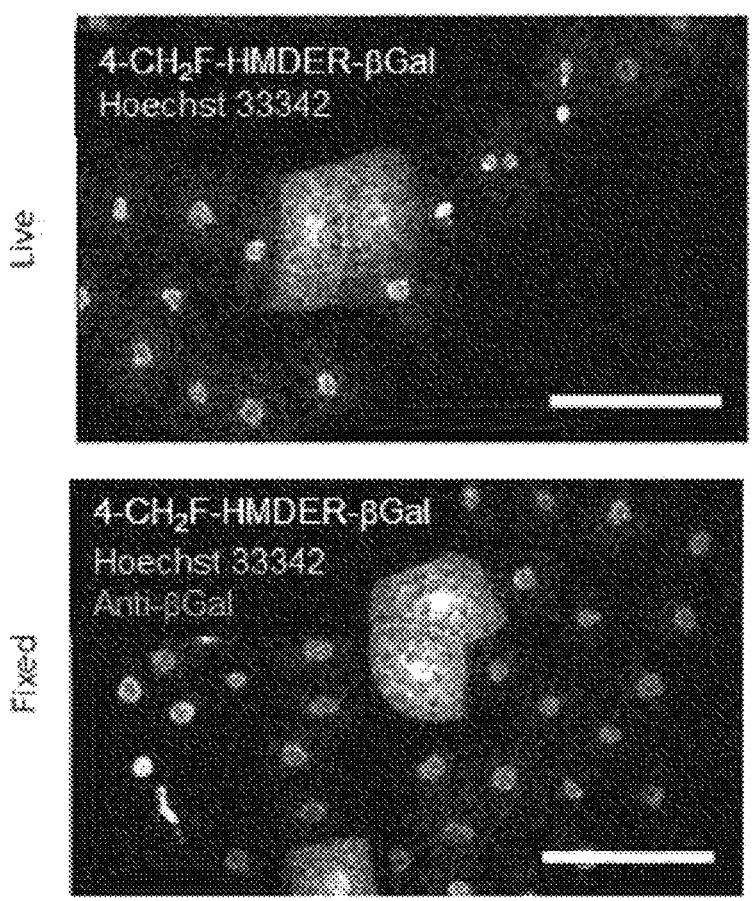

FIG. 14 A view indicating that the enzyme-specific retainable fluorescent compound of the present invention 4-CH₂F-HMDER-βGal can be applied in single-cell fluorescence imaging of β-galactosidase activity randomly expressed in a biological tissue.

Figure 15:
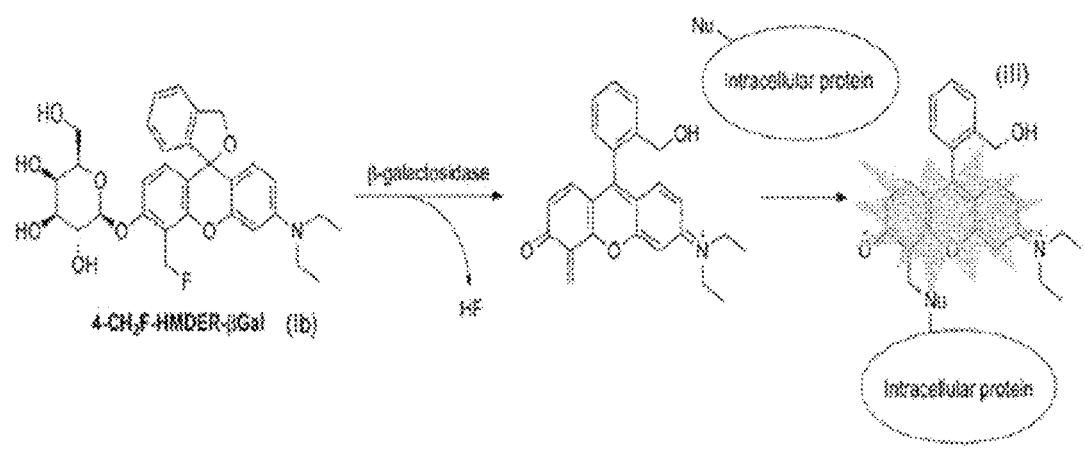

FIG. 15 A scheme showing the generation of a fluorescent compound (III) covalently bonded to an intracellular protein.

BEST MODE FOR CARRYING OUT THE INVENTION

Embodiments of the present invention are described below. The embodiments described below do not restrict the scope of the present invention, and changes other than according to the cited examples below may also be implemented as appropriate in a range not compromising the intent of the present invention.

In the present specification, an alkyl group or an alkenyl group may be any alkyl group or alkenyl group comprising a straight chain, a branched chain, a ring, or any combination thereof. The carbon number of the alkyl group or alkenyl group is not particularly limited, but is about C1-6, preferably about C1-4, and more preferably about C1 or C2. In the present specification, the alkyl group or alkenyl group may have one or more of any substituent. Alkoxy groups, halogen atoms (which may be fluorine atoms, chlorine atoms, bromine atoms, or iodine atoms), amino groups, mono- or di-substituted amino groups, substituted silyl groups, acyl groups, or aryl groups and the like can be cited as examples of substituents, but the possible substituents are not thus limited. When an alkyl group or alkenyl group has two or more substituents, the substituents may be the same or different. The same applies for the alkyl portions or alkenyl portions of other substituents which include an alkyl portion or an alkenyl portion (e.g., alkyloxy groups, aralkyl groups, and the like).

(1) Enzyme-Specific Retainable Fluorescent Compound

The enzyme-specific retainable fluorescent compound of the present invention, in one aspect thereof, is a compound having a structure represented by General Formula (I) below.

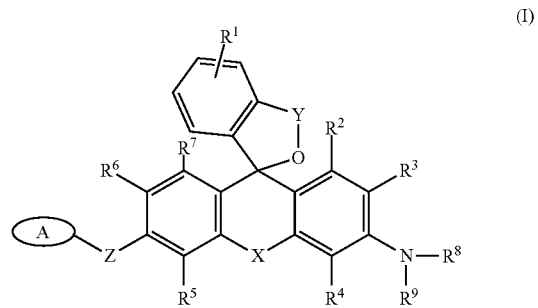

(I)

In General Formula (I) above, $R^1$ represents a hydrogen atom or one to four substituents bonded to the benzene ring. Alkyl groups, alkoxy groups, halogen atoms, amino groups, mono- or di-substituted amino groups, substituted silyl groups, or acyl groups and the like can be cited as examples of substituents, but the possible substituents are not thus limited. When there are two or more substituents on the benzene ring, the substituents may be the same or different. $R^1$ is more preferably a hydrogen atom, a lower alkyl group, or a lower alkoxy group. A hydrogen atom is particularly preferred.

In the formula, $R^3$, $R^4$, $R^5$, and $R^6$ each independently represent —$CFR^{10}R^{11}$ or —$CF_2R^{12}$, or a hydrogen atom, a hydroxyl group, an alkyl group, or a halogen atom, and $R^{10}$, $R^{11}$, and $R^{12}$ each independently represent a hydrogen atom, an alkyl group, or an alkenyl group. Furthermore, at least one of $R^3$, $R^4$, $R^5$, and $R^6$ herein represents —$CFR^{10}R^{11}$ or —$CF_2R^{12}$. At least one of $R^3$, $R^4$, $R^5$, and $R^6$ is preferably —$CFR^{10}R^{11}$. At least one of $R^3$, $R^4$, $R^5$, and $R^6$ is more preferably —$CH_2F$.

In the formula, $R^2$ and $R^7$ each independently represent a hydrogen atom, a hydroxyl group, an alkyl group, or a halogen atom. $R^2$ and $R^7$ are preferably hydrogen atoms.

In the formula, $R^8$ and $R^9$ each independently represent a hydrogen atom or an alkyl group. When $R^8$ and $R^9$ are both alkyl groups, the alkyl groups nay be the same or different. For example, $R^8$ and $R^9$ are preferably each independently a methyl group or an ethyl group, and a case in which any of $R^8$ and $R^9$ is an ethyl group is further preferred.

In the formula, X represents an oxygen atom, Se, $CR^{13}R^{14}$, or $SiR^{15}R^{16}$. $R^{13}$, $R^{14}$, $R^{15}$, and $R^{16}$ each independently represent a hydrogen atom or an alkyl group. Among the abovementioned substituents, an oxygen atom is preferred.

In the formula, Y represents a $C_{1-3}$ alkylene group. The alkylene group may be a straight-chain alkylene group or a branched-chain alkylene group. For example, a methylene group (—$CH_2$—), an ethylene group (—$CH_2$—$CH_2$—), or a propylene group (—$CH_2$—$CH_2$—$CH_2$—) may be used, as well as —$CH(CH_3)$—, —$CH_2$—$CH(CH_3)$—, —$CH(CH_2CH_3)$—, or the like as a branched-chain alkylene group. Among these substituents, a methylene group or an ethylene group is preferred, and a methylene group is more preferred.

In the formula, Z represents an oxygen atom or $NR^{17}$, and $R^{17}$ represents a hydrogen atom or an alkyl group. Among these substituents, an oxygen atom is preferred.

In the formula, group A represents a monovalent group which is cleaved by an enzyme, and specific examples thereof include a β-galactopyranosyl group, an α-mannosyl group, a β-N-acetylglucosamyl group, a βlactam group, a phosphoric acid ester, an aminophenoxy group, a hydroxyphenoxy group, γ-glutamic acid, and the like, but these examples are net limiting.

A reductase, oxidase, hydrolase, or the like can be cited as an example of an enzyme for cleaving group A, and a reporter enzyme or an enzyme specifically expressed or activated in cancer cells can be cited as an example thereof. More specifically, a β-galactosidase, β-lactamase, α-mannosidase, esterase, alkali phosphatase, luciferase, peroxidase, cytochrome P450 oxidase, β-glucosidase, β-glucuronidase, β-hexosaminidase, lactase, γ-glutamyl transferase, or the like can be cited as an example thereof, but these examples are not limiting. A β-galactosidase, β-lactamase, alkali phosphatase, luciferase, β-hexosaminidase, peroxidase, or γ-glutamyl transferase is preferred. A β-galactosidase is most preferred.

The compound represented by Formula (I) above (including the aspects of Formulas (I') and (Ia) through (Ic); the same hereinafter) sometimes exists as a salt. Base addition salts, acid addition salts, amino acid salts, and the like can be cited as examples thereof. Sodium salts, potassium salts, calcium salts, magnesium salts, and other metal salts; ammonium salts; or triethylamine salts, piperidine salts, morpholine salts, and other organic amine salts can be cited as examples of base addition salts; and hydrochlorides, sulfates, nitrates, and other mineral acid salts; and salts of methanesulfonic acid, p-toluenesulfonic acid, citric acid, oxalic acid and other organic acids can be cited as examples of acid addition salts. Glycinates and the like can be cited as examples of amino acid salts. The salt of the compound of the present invention is, of course, not limited to these examples.

The compound represented by Formula (I) sometimes has one or more asymmetric carbons, depending on the types of substituents, and an optical isomer, diastereomer, or other stereoisomer may exist. Any stereoisomer in pure form, any mixture of stereoisomers, a racemate thereof, or the like is included in the scope of the present invention.

The compound represented by Formula (I) or the salt thereof may exist as a hydrate or solvate, but these substances are both included in the scope of the present invention. The type of solvent for forming a solvate is not particularly limited, but ethanol, acetone, isopropanol, and other solvents can be cited as examples thereof.

In the examples of the present specification, manufacturing methods are specifically described for representative compounds included as the compound of the present invention represented by General Formula (I), and a person skilled in the art could easily manufacture any compound included by General Formula (I) by referring to the disclosure of the present specification and appropriately selecting starting materials or reagents, reaction conditions, and the like as needed.

(2) Mechanisms of Fluorescence Emission and Intracellular Retention of the Compound of the Present Invention When the enzyme-specific retainable fluorescent compound represented by Formula (I) provided by the present invention is taken into a cell, in a cell in which an enzyme capable of cleaving the group represented by A is expressed, the group represented by A is cleaved in the cell, hydrogen fluoride is released from the —$CFR^{10}R^{11}$ or —$CF_2R^{12}$ positioned at $R^3$, $R^4$, $R^5$, or $R^6$, and a quinone methide is generated. Because the quinone methide is rapidly subjected to attack by surrounding nucleophiles, when a quinone methide is generated in the cell, the quinone methide is thought to rapidly react with nucleophilic groups of surrounding proteins and become irreversibly bonded to the proteins.

For example, in the case of the compound represented by Formula (Ib), β-galactosidase causes cleavage of group A and ring-opening of a spiro ring, aid a fluorescent, compound (III) covalently bonded to an intracellular protein is generated. The detailed mechanism of fluorescence in a compound similar to Formula (III) is known to those skilled in the art, as disclosed International Publication 2005/024049.

A compound represented by General Formula (I) or a salt thereof exhibits almost no fluorescence when irradiated with excitation light in a neutral range, e.g., excitation light having a wavelength of about 440 to 550 nm, but a ring-opened compound formed by enzyme activity has the property of emitting extremely strong fluorescence under the same conditions. Consequently, when a cell having taken in the enzyme-specific retainable fluorescent compound represented by Formula (I) does not express an enzyme capable of cleaving the group represented by A, a ring-opened compound such as the one represented by Formula (III) is not generated, and a fluorescent substance is not generated in the cell. Thus, through use of the enzyme-specific retainable fluorescent compound represented by Formula (I), fluorescence is selectively generated only in a cell in which an enzyme capable of cleaving the group represented by A is expressed and activated. Furthermore, because the reaction product compound represented by Formula (III) or the like is covalently bonded to an intracellular protein, leakage thereof to the outside of the cell is suppressed, and it is thereby possible to visualize, specifically and at a single-cell level of detail, a cell in which the enzyme is expressed and activated.

From the characteristics described above, the compound represented by Formula (I) of the present invention makes it possible for a cell to be visualized at a single-cell level of detail without immobilization thereof or after immobilization thereof, and has a wide range of usage applications including use thereof as a tool for cell biological research in cell lines as a fluorescence probe, as well as a test drug, diagnostic drug, or the like used for rapid pathologic examination in surgical settings for cancer and the like.

(3) Method for Selective Cell Visualization Using the Enzyme-Specific Retainable Fluorescent Compound of the Present Invention The fluorescent compound capable of being retained in cells of the present invention exhibits the characteristics described above, and can therefore be used in a method for cell-specific visualization of a target cell in which a specific enzyme is expressed. Specifically, a step is performed for bringing the enzyme-specific retainable fluorescent compound of Formula (I) into contact with β-galactosidase or another enzyme specifically expressed in a target cell, and a step is then performed for detecting fluorescence that occurs in response to irradiation with excitation light, and it is thereby possible to specifically visualize only the target cell in which the β-galactosidase or the like is expressed.

Means for bringing the fluorescent compound retainable in cells of the present invention into contact with the enzyme specifically expressed in the target cell include, as representative examples, sample addition, coating, or spraying of a solution comprising the enzyme-specific retainable fluorescent compound, but the means can be selected as appropriate for the application. When the fluorescent compound retainable in cells of the present invention is applied for diagnosis or assisting in diagnosis in an animal individual, or for detecting a specific cell or tissue therein, the means for bringing the compound into contact with the enzyme expressed in the target cell or tissue is not particularly limited, and intravenous administration, for example, or another administration means common in the relevant field may be used.

Photoirradiation of the target cell may be performed by radiating light directly or via a waveguide (optical fiber or the like) to the target cell. Any light source can be used that, is capable of radiating light which includes the wavelength absorbed by the enzyme-specific retainable fluorescent compound of the present invention after enzymatic cleavage thereof, and the light source can be appropriately selected in accordance with such factors as the environment in which the method of the present invention is performed.

The enzyme-specific retainable fluorescent compound of the present invention may be used without modification as the compound represented by General Formula (I) or a salt thereof, or may, as needed, be used as a composition obtained by blending additives normally used for preparing reagents. For example, solubilizers, pH adjusters, buffer agents, isotonizing agents, and other additives for enabling a reagent to be used in a physiological environment can be used, and the blended amounts of these additives can appropriately be selected by a person skilled in the art. The resultant composition is commonly provided as a mixture in powder form, a freeze-dried product, granules, a tablet, a liquid, or other appropriate form of the composition, but can be dissolved for application in distilled water for injection or an appropriate buffer solution at the time of use.

EXAMPLES

The present invention will next be described in further detail using examples, but the examples are not limiting of the present invention.

(1) The enzyme-specific retainable fluorescent compounds of the present invention 2-CHF$_2$-HMDER-βgal, 4-CHF$_2$-HMDER-βGal, and 4-CH$_2$F-HMDER-βGal were synthesized in accordance with schemes 1 through 3 described below.

Scheme 1: Synthesis of 2-CHF$_2$—HMDER-βGal

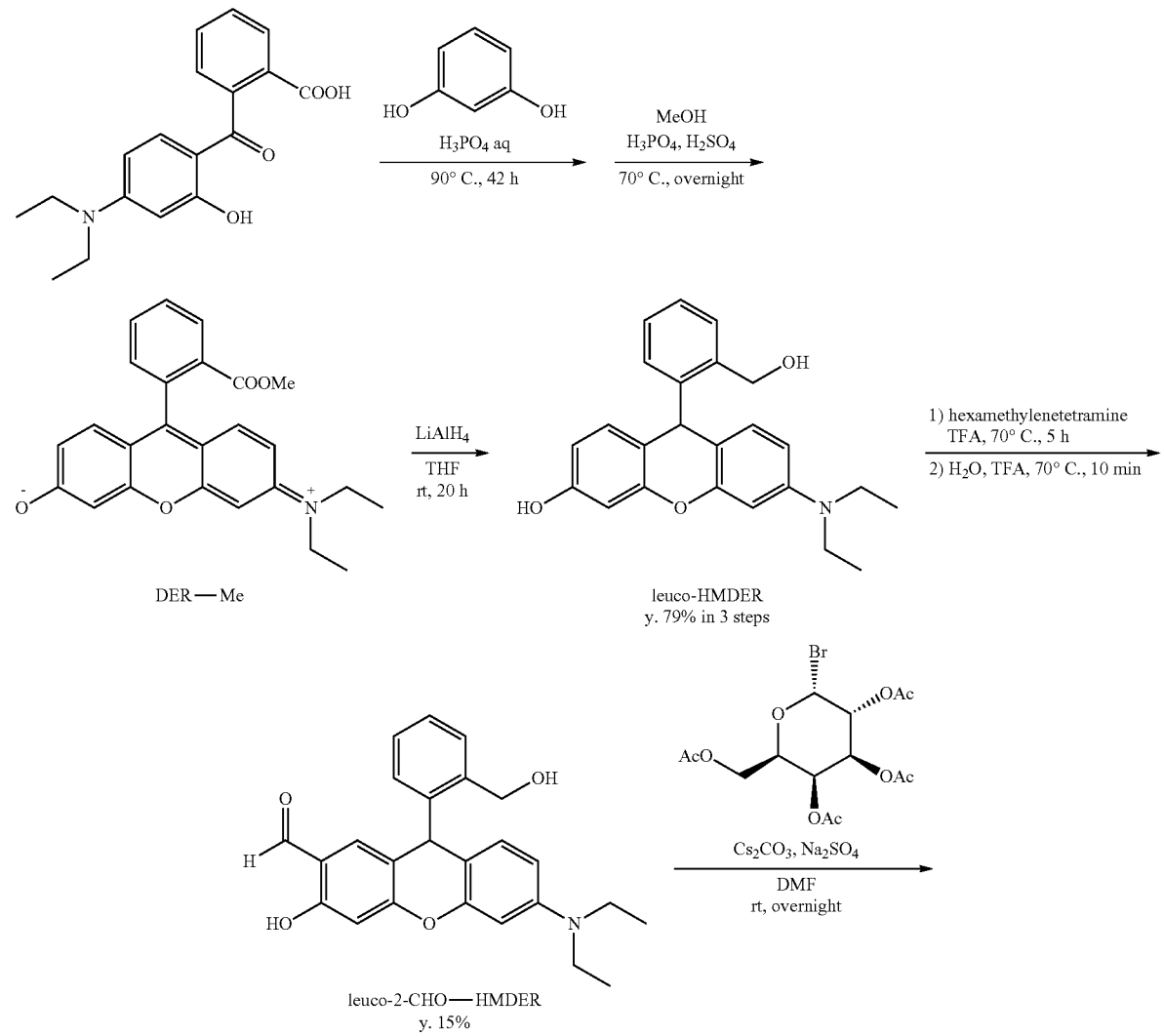

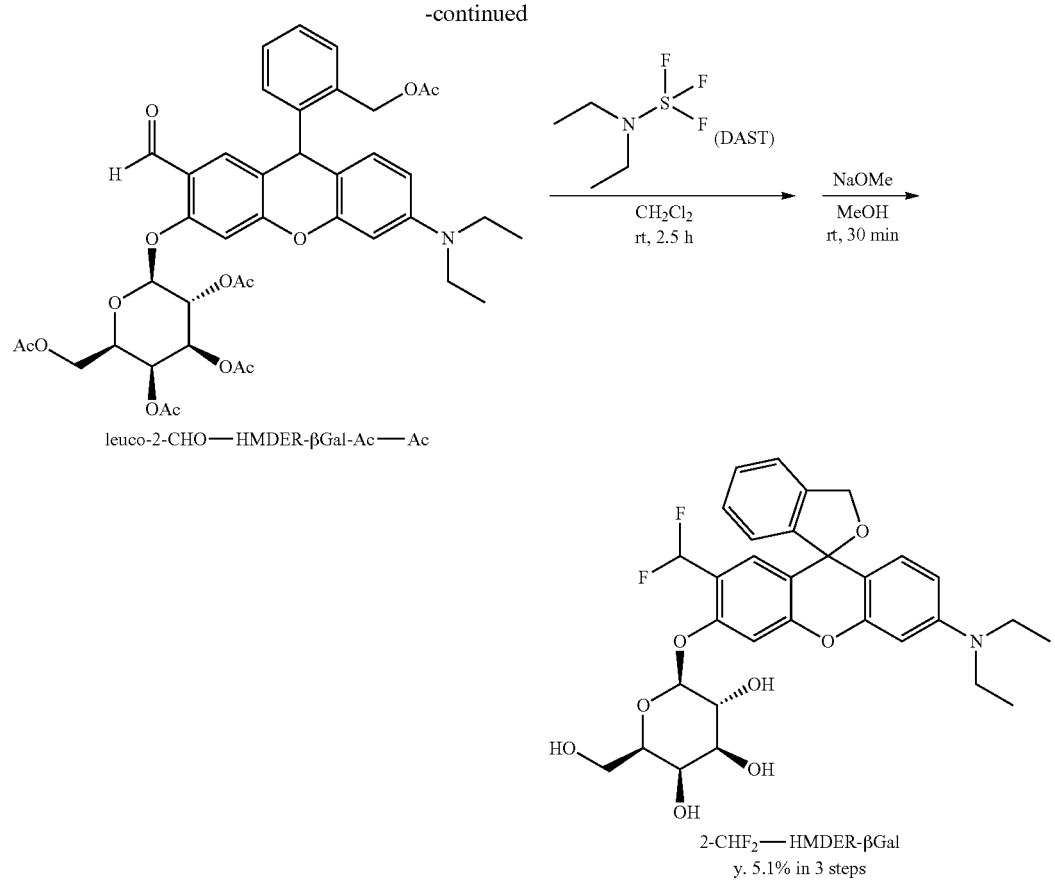
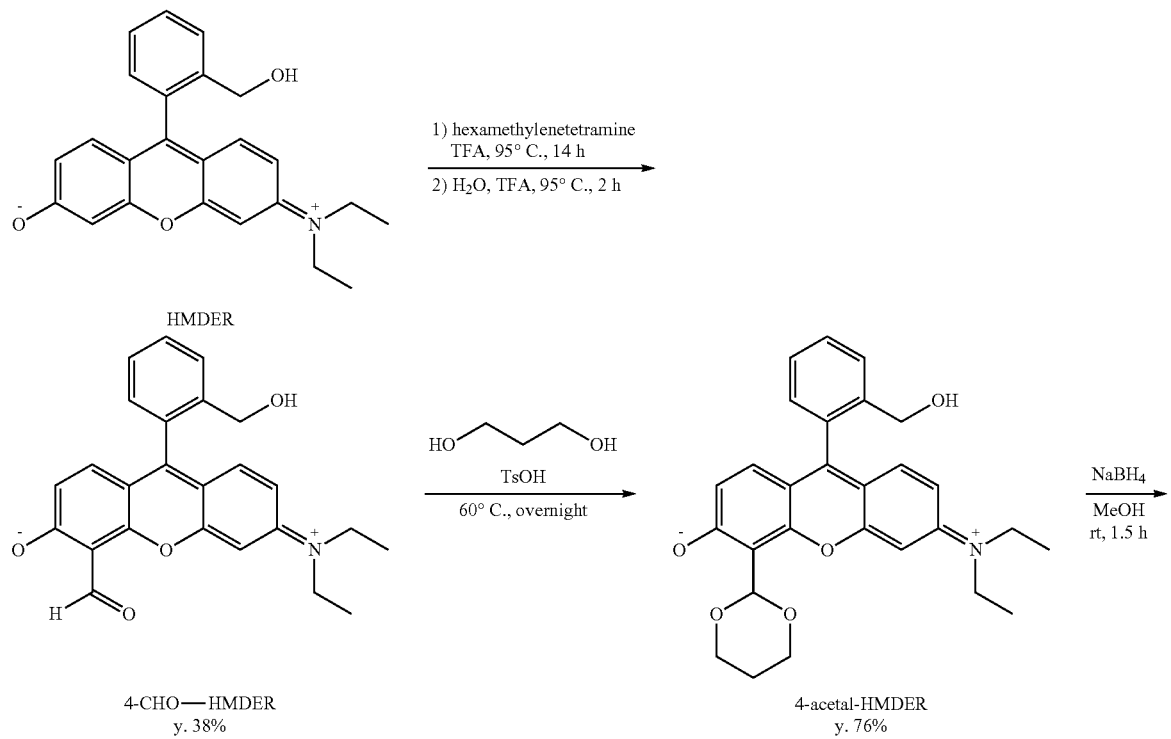
Scheme 2: Synthesis of 4-CHF$_2$—HMDER-βGal

-continued
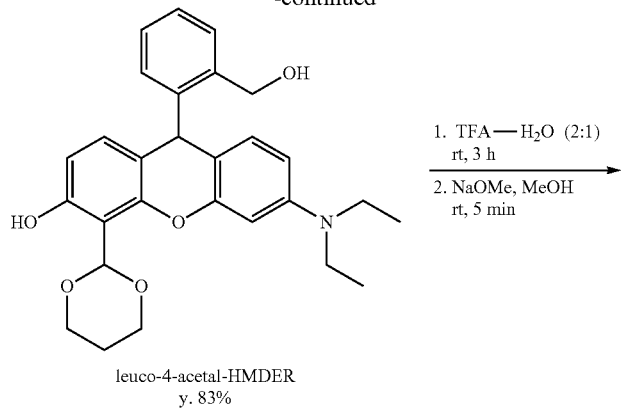
leuco-4-acetal-HMDER
y. 83%
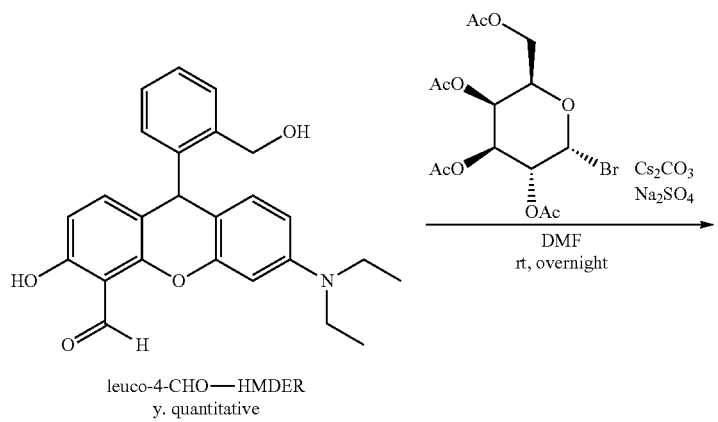
leuco-4-CHO—HMDER
y. quantitative
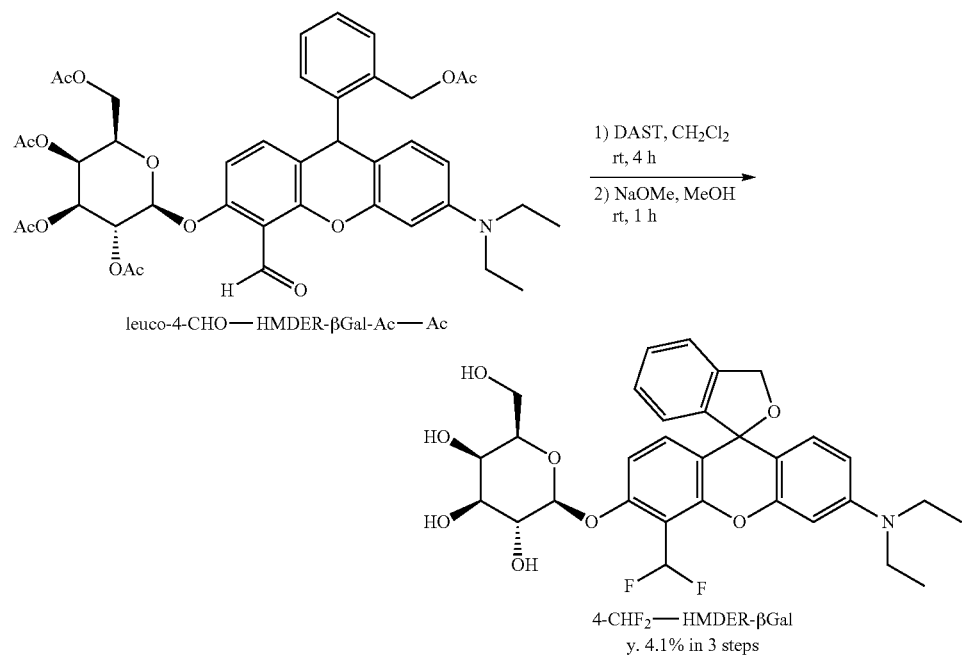
leuco-4-CHO—HMDER-βGal-Ac—Ac
4-CHF₂—HMDER-βGal
y. 4.1% in 3 steps Scheme 3: Synthesis of 4-CH$_2$F—HMDER-βGal
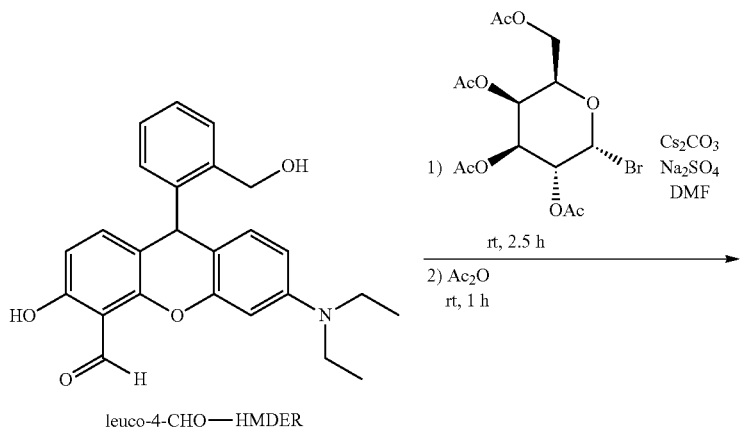
leuco-4-CHO—HMDER
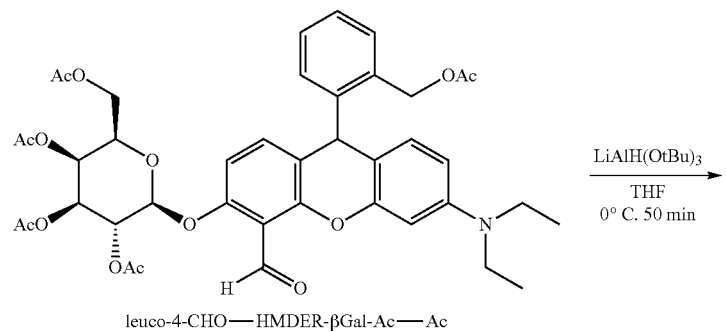
leuco-4-CHO—HMDER-βGal-Ac—Ac
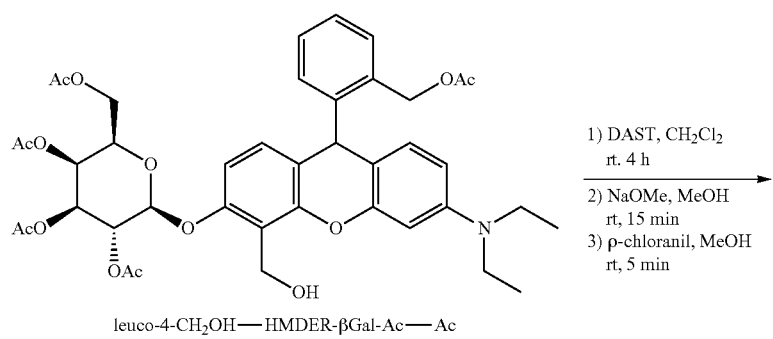
leuco-4-CH$_2$OH—HMDER-βGal-Ac—Ac
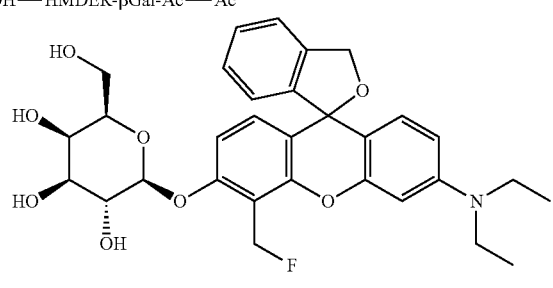
4-CH$_2$F—HMDER-βGal
y. 18% in 6 steps The details of the synthesis reactions are described below.

○ Synthetic Reagents, Apparatus, and the Like Used

Commercially available starting materials were procured from reagent manufacturers (Wako Pure Chemical industries, Ltd., Tokyo Chemical Industry Co., Ltd., and Sigma-Aldrich Co., Ltd.).

Column and Apparatus Used for Purification by High-Speed Liquid Chromatography

Pump: PU-2080 and PU-2087 (JASCO Corporation)

Detector: MD-2010 (JASCO Corporation)

Column: Inertsil ODS-3 (10×250 mm or 20×250 mm, GL Science Inc.)

Solvent Used in Separation and Purification by HPLC
A: 100 mM triethylamine acetate
B: 99% acetonitrile, 1% Milli-Q Solution feeding in HPLC separation was performed at 25 mL/minute (pump: PU-2087, column: 20×250 mm) and 5 mL/minute (pump: PU-2080, column: 10×250 mm).

Purification by medium-pressure column chromatography was performed using a YFLC-AI580 (Yamazen Corporation).

NMR measurement was performed using an AVANCE III 400 Nanobay (Bruker Co., Ltd.). (400 MHz for $^1$H NMR and 101 MHz for $^{13}$C NMR)

Mass spectrometry was performed using a micrOTOF (ESI-TOF, Bruker Co., Ltd.). For high-resolution MS (HRMS) measurement, sodium formate was used as the external standard substance.

Explanation of Abbreviations

THF: tetrahydrofuran
DMF: N,N-dimethylformamide
TFA: trifluoroacetic acid
DAST: N,N-diethylaminosulfur trifluoride
PLC: thin-layer plate for fractionation (Synthesis Example 1) Synthesis of 6-(diethylamino)-9-(2-(hydroxymethyl)phenyl)-9H-xanthen-3-ol (leuco-HMDER)

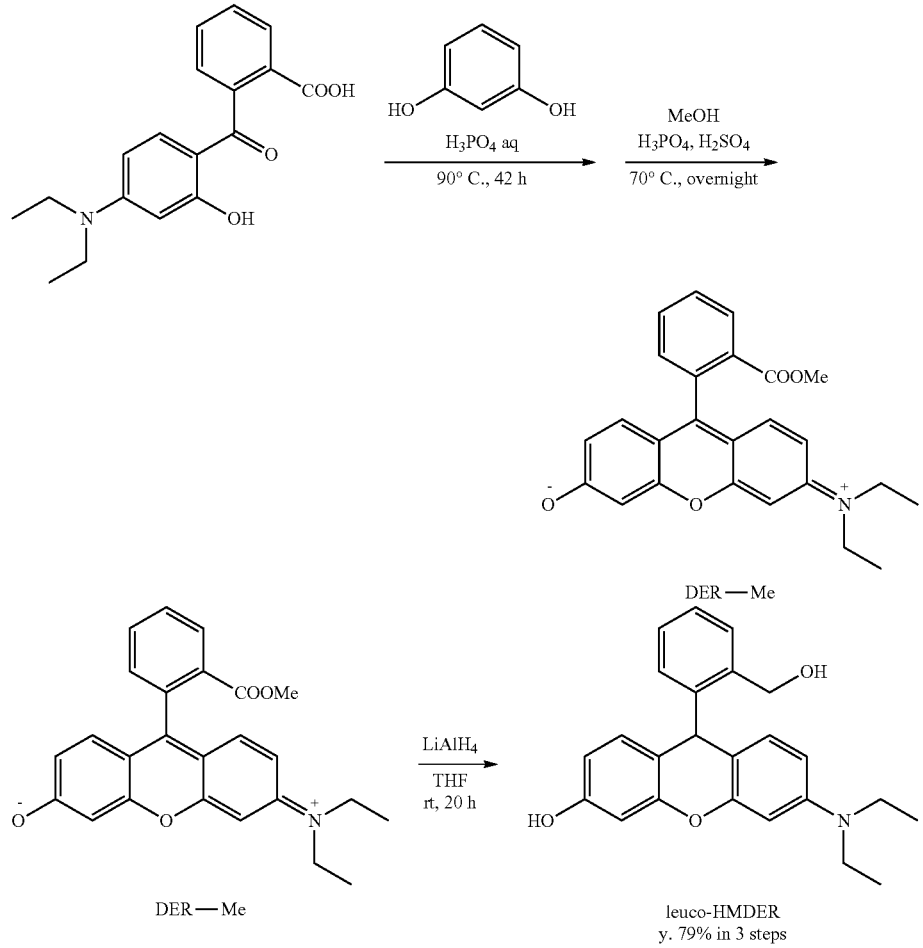

2-(4-diethylamino-2-hydroxybenzoyl)benzoic acid (2.54 g, 8.05 mmol), resorcinol (900 mg, 8.17 mmol), and 85% $H_3PO_4$ (15 mL) were stirred for 42 hours at a temperature of 90° C. After the moisture was removed therefrom by evaporation, MeOH (60 mL, 47.5 g, 1483 mmol) and $H_2SO_4$ (13.5 mL, 24.8 g, 253 mmol) were added, and the mixture was stirred overnight at 70° C. The MeOH was removed by evaporation, and a saturated aqueous solution of $NaHCO_3$ was added for neutralization. $CH_2Cl_2$ was added and liquid separation was performed three times, $Na_2SO_4$ was added to the organic phase and the product was dried, the solvent was removed by evaporation, and DER-Me was obtained as a red solid. In an argon atmosphere, LiAlH$_4$ (1680 mg, 44.3 mmol) and anhydrous THF (80 mL) were added, and the mixture was stirred for 20 hours at room temperature. A saturated aqueous solution of Rochelle salt was added under ice cooling and the mixture was stirred for 1 hour, EtOAc was added and liquid separation was performed three times, Na$_2$SO$_4$ was added to the organic phase and the product was dried, and the solvent was removed by evaporation. The resultant residue was purified by medium-pressure silica gel column chromatography (eluent: CH$_2$Cl$_2$/MeOH=98/2), and the desired compound leuco-HMDER was obtained as a pink solid (2.40 g with a yield of 79% in three steps).

$^1$H NMR (CDCl$_3$): δ. 7.31-7.29 (m, 1H), 7.14 (brs, 3H), 6.61-6.56 (m, 2H), 6.48 (d, 1H, J=2.0 Hz), 6.34 (d, 1H, J=2.3 Hz), 6.23-6.21 (m, 2H), 5.25 (s, 1H), 4.55-4.45 (m, 2H), 3.23 (q, 4H, J=7.0 Hz), 1.07 (t, 6H, J=7.0 Hz). $^{13}$C NMR (CDCl$_3$): δ. 155.8, 151.5, 151.3, 147.9, 144.7, 137.7, 131.4, 130.3, 130.0, 129.5, 128.3, 127.0, 116.3, 111.3, 111.0, 108.0, 103.3, 99.2, 62.9, 44.4, 39.8, 12.5. HRMS-ESI (m/z): [M+Na]$^+$ calculated for 398.1727 (C$_{24}$H$_{25}$NNaO$_3$), found 398.1722.

(Synthesis Example 2) Synthesis of 6-(diethylamino-3-hydroxy-9-(2-(hydroxymethyl)phenyl)-9H-xanthene-2-carbaldehyde(leuco-2-CHO-HMDER)

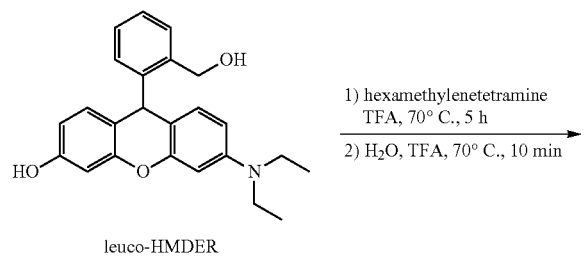

leuco-HMDER 1) hexamethylenetetramine TFA, 70° C., 5 h
2) H$_2$O, TFA, 70° C., 10 min

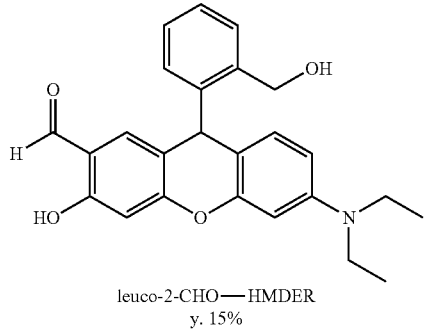

leuco-2-CHO—HMDER
y. 15%

In an argon atmosphere, leuco-HMDER (2.20 g, 5.86 mmol), hexamethylenetetramine (838 mg, 5.98 mmol), and TFA (10 mL) were stirred for 5 hours at 70° C., and H$_2$O (10 mL) was added and the mixture was stirred for 10 minutes at 70° C. The TFA and the H$_2$O were removed by evaporation. A saturated aqueous solution of NaHCO$_3$ was added for neutralization, EtOAc was added, liquid separation was performed three times, and the organic phase was concentrated by evaporation. The product was purified by medium-pressure silica gel column chromatography (eluent: CH$_2$Cl$_2$/MeOH=98/2), and the desired compound leuco-2-CHO-HMDER was obtained as a pink solid (344 mg with a yield of 15%).

$^1$H NMR (CDCl$_3$): δ. 11.09 (s, 1H), 9.53 (d, 1H, J=0.4 Hz), 7.43-7.41 (m, 1H), 7.27-7.25 (m, 2H), 7.19-7.16 (m, 1H), 7.11 (d, 1H, J=0.9 Hz), 6.67 (dd, 1H, J=0.5 and 8.7 Hz), 6.64 (s, 1H), 6.39 (d, 1H, J=2.6 Hz), 6.31 (dd, 1H, J=2.6 and 8.7 Hz), 5.45 (s, 1H), 4.75-4.59 (m, 2H), 3.32 (q, 4H, J=7.1 Hz), 1.15 (t, 6H, J=7.1 Hz). $^{13}$C NMR (CDCl$_3$): δ. 194.9, 161.9, 157.9, 150.8, 148.2, 144.4, 138.1, 136.1, 31.4, 130.0, 129.4, 128.8, 127.4, 118.2, 117.5, 110.2, 108.6, 104.2, 98.9, 63.3, 44.5, 38.8, 12.7. HRMS-ESI (m/z): [M+H]+ calculated for 404.1856 (C$_{25}$H$_{26}$NO$_4$), found 404.1845.

(Synthesis Example 3) Synthesis of (2S,3R,4S,5R,6R)-2-((6'-(diethylamino)-2'-(difluoromethyl)-3H-spiro[isobenzofuran-1,9'-xanthen]-3'-yl)oxy)-6-(hydroxymethyl)tetrahydro-2H-pyran-3,4,5-triol(2-CHF$_2$-HMDER-βGal)

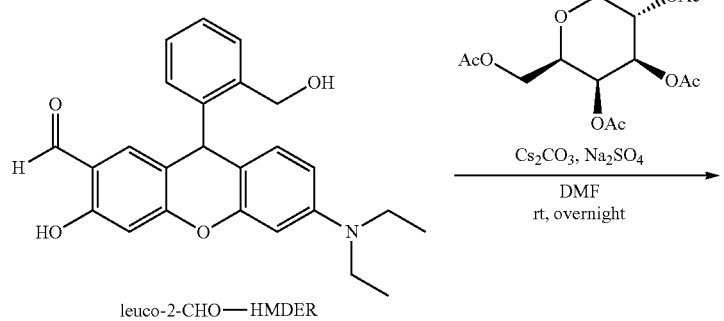

leuco-2-CHO—HMDER

Cs$_2$CO$_3$, Na$_2$SO$_4$
DMF
rt, overnight

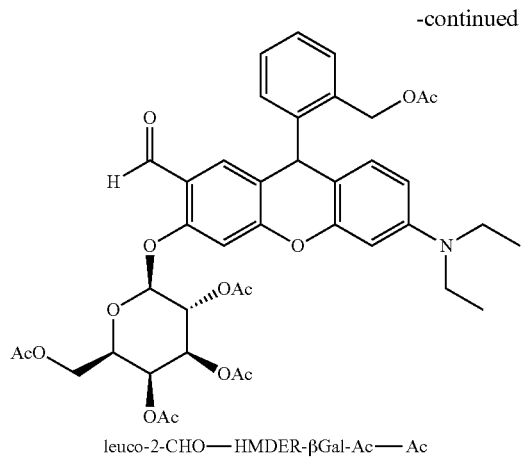
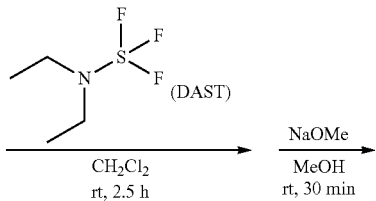

leuco-2-CHO—HMDER-βGal-Ac—Ac

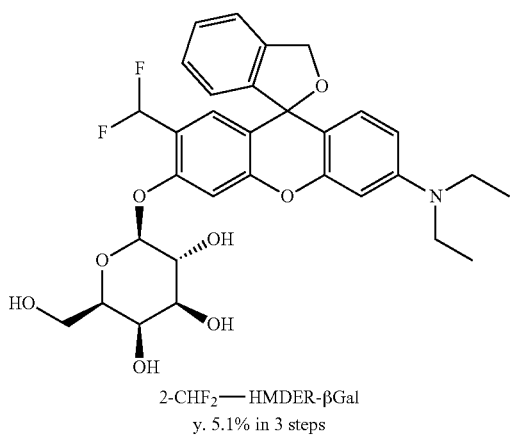

2-CHF$_2$—HMDER-βGal
y. 5.1% in 3 steps

Synthesis of 2,3,4,6-tetra-O-acetyl-α-D-galactopyranosyl bromide was performed as previously reported in (J. L. Montero et al., Carbohydr. Res. 1997, 297, 175.). In an argon atmosphere, leuco-2-CHO-HMDER (210 mg, 0.520 mmol), 2,3,4,6-tetra-O-acetyl-α-D-galactopyranosyl bromide (260 mg, 0.632 mmol), Cs$_2$CO$_3$ (293 mg, 0.899 mmol), Na$_2$SO$_4$ (321 mg, 2.26 mmol), and DMF (1 mL) were stirred overnight at room temperature. The DMF was removed by evaporation, CH$_2$Cl$_2$ and a saturated aqueous solution of NH$_4$Cl were added and liquid separation was performed three times, Na$_2$SO$_4$ was added to the organic phase, the product was dried, and the product was concentrated by evaporation. The resultant residue was purified by medium-pressure silica gel column chromatography (eluent: CH$_2$Cl$_2$/EtOAc=98/2), and leuco-2-CHO-HMDER-βGal-Ac—Ac (137 mg, 0.177 mmol) was obtained. In an argon atmosphere, the product was dissolved in anhydrous CH$_2$Cl$_2$ (5 mL), DAST (300 μL, 366 mg, 2.27 mmol) was added, and the mixture was stirred for two and a half hours at room temperature. MeOH (10 mL) was added under ice cooling to quench the reaction, and the solvent was removed by evaporation. MeOH (28 mL) was added to dissolve the resultant residue, NaOMe 11.38 g, 25.5 mmol) was added, and the product was stirred for 30 minutes at room temperature. The solvent was removed by evaporation, CH$_2$Cl$_2$ was added to the residue and celite filtration was performed, and the filtrate was concentrated by evaporation. The product was purified by medium-pressure silica gel column chromatography (eluent: CH$_2$Cl$_2$/MeOH=97/3 to 96/4) and PLC (eluent: CH$_2$Cl$_2$/MeOH=9/1), and the desired compound 2-CHF$_2$-HMDER-βGal was obtained as a pale purple solid (15.2 mg with a yield of 5.1% in three steps).

$^1$H NMR (CD3OD): δ. 7.46-7.39 (m, 2H), 7.30 (t, 1H, J=7.3 Hz), 7.14 (s, 0.5H), 7.13 (s, 0.5H), 7.07 (s, 1H), 7.03 (t, 0.5H, J=55.5 Hz), 7.02 (t, 0.5H, J=55.5 Hz), 6.84 (d, 0.5H, J=7.6 Hz), 6.83 (d, 0.5H, J=7.6 Hz), 6.72 (d, 0.5H, J=8.8 Hz), 6.72 (d, 0.5H, J=8.8 Hz), 6.47-6.43 (m, 2H), 5.26 (s, 2H), 4.97 (dd, 1H, J=7.8 and 11.5 Hz), 3.94 (d, 1H, J=2.6 Hz), 3.86-3.78 (m, 4H), 3.63-3.60 (m, 1H), 3.38 (q, 4H, J=7.0 Hz), 1.15 (t, 6H, J=7.0 Hz). $^{13}$C NMR (CD$_3$OD): δ. 157.2 (t, J=5.5 Hz), 154.7, 154.6, 152.9, 152.9, 150.3, 145.8, 145.7, 140.4, 140.3, 130.7, 129.5, 129.4, 128.0-127.8 (m), 124.7, 124.7, 122.0, 121.0 (t, J=22.9 Hz), 120.9 (t, J=22.9 Hz), 120.7, 120.6, 112.5 (t, J=234.2 Hz), 112.1, 109.9, 104.7, 104.6, 103.5, 103.4, 98.6, 85.2, 85.2, 77.3, 74.8, 72.7, 72.7, 72.1, 70.2, 62.4, 45.4, 12.8. HRMS-ESI (m/z): [M+Na]$^+$ calculated for 608.2066 (C$_{31}$H$_{33}$F$_2$NNaO$_8$), found 608.2075.

(Synthesis Example 4) Synthesis of 3-(diethylimino)-5-formyl-9-(2-(hydroxymethyl)phenyl)-3H-xanthen-6-olate(4-CHO-HMDER)

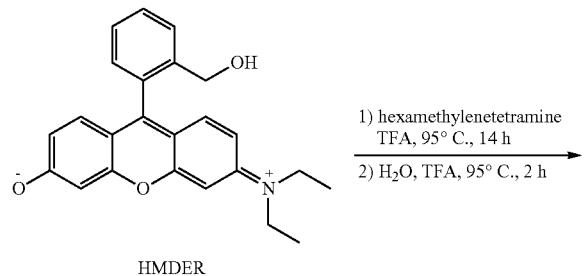

(Synthesis Example 5) Synthesis of 3-(diethylimino)-5-(1,3-dioxan-2-yl)-9-(2-(hydroxymethyl)phenyl)-3H-xanthen-6-olate(4-acetal-HMDER)

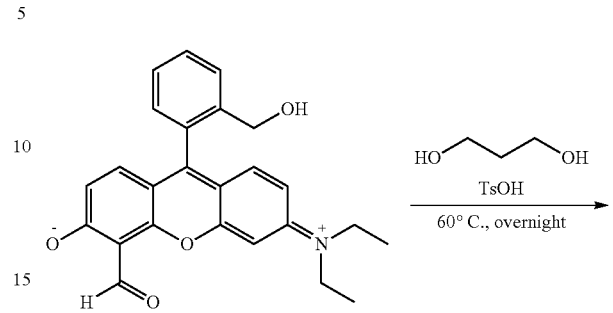

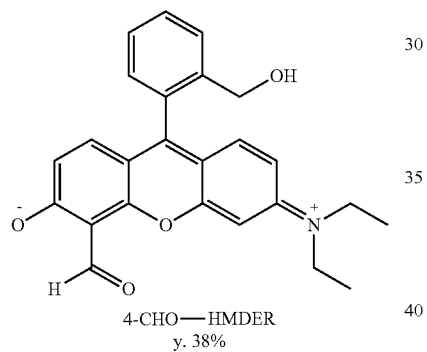

4-CHO—HMDER
y. 38%

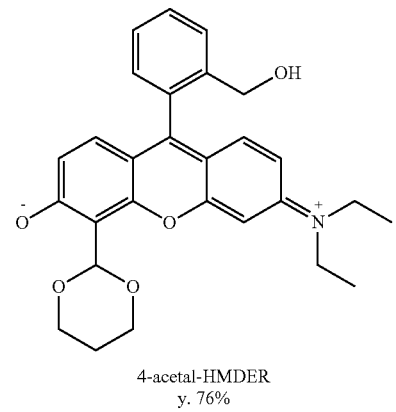

4-acetal-HMDER
y. 76%

Synthesis of HMDER was performed with reference to the previously reported method (M. Kamiya et al., J. Am. Chem. Soc. 2011, 133, 12960.). Hexamethylenetetramine (694 mg, 6.38 mmol) and TFA (6 mL) were added to HMDER (2.35 g, 6.29 mmol) and the mixture was stirred for 14 hours at 95° C., H$_2$O (10 mL) was added, and the mixture was stirred for 2 hours at 95° C. The TFA and H$_2$O were removed by evaporation, CH$_2$Cl$_2$ and a saturated aqueous solution of NaHCO$_3$ were added and liquid separation was performed three times, and the organic phase was concentrated by evaporation. The residue was purified by medium-pressure silica gel column chromatography (eluent: CH$_2$Cl$_2$/MeOH=98/2), and the desired compound 4-CHO-HMDER was obtained as a red solid (963 mg with a yield of 38%).

$^1$H NMR (CDCl$_3$): δ. 12.09 (s, 1H), 10.67 (s, 1H, CHO), 7.35-7.34 (m, 2H), 7.27-7.23 (m, 1H), 7.07 (d, 1H, J=8.8 Hz), 6.91 (d, 1H, J=7.6 Hz), 6.75 (d, 1H, J=8.7 Hz), 6.57 (d, 1H, J=8.8 Hz), 6.44 (d, 1H, J=2.5 Hz), 6.41 (dd, 1H, J=2.5 and 8.7 Hz), 5.25 (d, 2H, J=5.4 Hz), 3.33 (q, 4H, J=7.1 Hz), 1.15 (t, 6H, J=7.1 Hz). $^{13}$C NMR (CDCl$_3$): δ 193.9, 163.3, 152.6, 150.8, 148.8, 144.4, 139.5, 138.6, 129.6, 128.4, 128.2, 123.9, 120.8, 115.9, 112.5, 111.0, 109.0, 108.8, 97.4, 83.1, 71.7, 44.4, 12.6. HRMS-ESI (m/z): [M+H]$^+$ calculated for 402.1700 (C$_{25}$H$_{24}$NO$_4$), found 402.1684.

Propane-1,3-diol (12 mL, 12.7 g, 167 mmol) and p-toluenesulfonic acid (27 mg, 0.157 mmol) were added to 4-CHO-HMDER (745 mg, 1.86 mmol) and the mixture was stirred overnight at 60° C. A saturated aqueous solution of NaHCO$_3$ was added to neutralize the product, CH$_2$Cl$_2$ was added, liquid separation was performed three times, and the organic phase was concentrated by evaporation. The resultant residue was purified by medium-pressure silica gel column chromatography (eluent: CH$_2$Cl$_2$/MeOH=98/2), and the desired compound 4-acetal-HMDER was obtained as a red solid (648 mg with a yield of 76%).

$^1$H NMR (CDCl$_3$): δ. 8.45 (s, 1H), 7.34-7.30 (m, 2H), 7.25-7.21 (m, 1H), 6.88 (d, 1H, J=7.6 Hz), 6.79 (d, 1H, J=8.7 Hz), 6.72 (d, 1H, J=8.5 Hz), 6.56 (d, 1H, J=8.7 Hz), 6.39-6.36 (m, 3H), 5.22 (s, 2H), 4.36-4.30 (m, 2H), 4.18-4.11 (m, 2H), 3.34 (q, 4H, J=7.0 Hz), 2.36-2.24 (m, 1H), 1.52 (d, 1H, J=13.7 Hz), 1.15 (t, 6H, J=7.0 Hz). $^{13}$C NMR (CDCl$_3$): δ. 156.9, 151.6, 148.7, 148.6, 145.0, 139.6, 131.0, 129.5, 128.2, 127.8, 124.1, 120.6, 116.6, 112.5, 111.6, 109.2, 108.6, 99.1, 97.8, 83.9, 71.5, 68.0, 67.8, 44.4, 25.9, 12.7. HRMS-ESI (m/z): [M+H]$^+$ calculated for 460.2119 (C$_{28}$H$_{30}$NO$_5$), found 460.2120.

(Synthesis Example 6) Synthesis of 6-(diethylamino)-4-(1,3-dioxan-2-yl)-9-(2-hydroxymethyl)phenyl)-9H-xanthen-3-ol(leuco-4-acetal-HMDER)

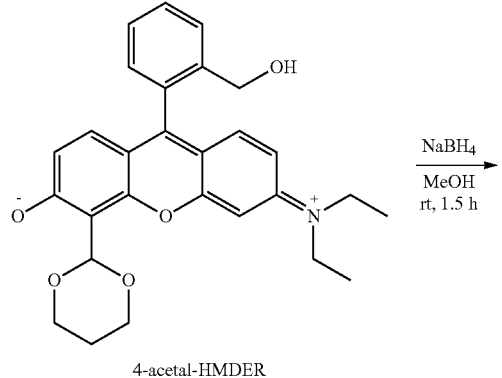

4-acetal-HMDER

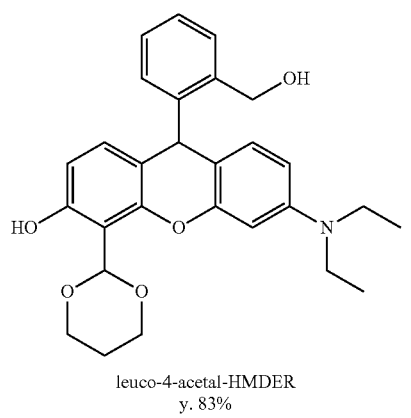

leuco-4-acetal-HMDER
y. 83%

In an argon atmosphere, MeOH (5 mL) and NaBH$_4$ (81 mg, 2.14 mmol) were added to 4-acetal-HMDER (182 mg, 0.396 mmol) and the mixture was stirred for 1 hour at room temperature. The solvent was removed by evaporation, a saturated aqueous solution of NaHCO$_3$ was added to quench the reaction, CH$_2$Cl$_2$ was added, and liquid separation was performed twice. The organic phase was concentrated by evaporation, and the desired compound leuco-4-acetal-HMDER was obtained as a pale pink solid (151 mg with a yield of 83%).

$^1$H NMR (CDCl$_3$): δ. 8.30 (s, 1H), 7.39-7.35 (m, 1H), 7.22-7.15 (m, 3H), 6.72 (d, 1H, J=8.6 Hz), 6.65 (d, 1H, J=8.6 Hz), 6.46 (d, 1H, J=8.6 Hz), 6.35 (d, 1H, J=2.5 Hz), 6.34 (s, 1H), 6.27 (dd, 1H, J=2.5 and 8.6 Hz), 5.33 (s, 1H), 4.60-4.50 (m, 2H), 4.34-4.31 (m, 2H), 4.14 (t, 2H, J=12.0 Hz), 3.30 (q, 4H, J=7.0 Hz), 2.35-2.23 (m, 1H), 1.80 (brs, 1H), 1.52 (d, 1H, J=13.7 Hz), 1.14 (t, 6H, J=7.0 Hz). $^{13}$C NMR (CDCl$_3$): δ. 155.8, 151.1, 148.3, 147.9, 144.5, 138.3, 131.4, 131.2, 129.9, 129.2, 128.2, 127.0, 115.9, 112.0, 111.2, 109.7, 108.2, 99.1, 98.9, 67.9, 67.9, 63.0, 44.3, 39.6, 25.9, 12.7. HRMS-ESI (m/z) [M+H]$^+$ calculated for 462.2275 (C$_{28}$H$_{32}$NO$_5$), found 462.2278.

(Synthesis Example 7) Synthesis of 6-(diethylamino)-3-hydroxy-9-(2-hydroxymethyl)phenyl)-9H-xanthene-4-carbaldehyde(leuco-4-CHO-HMDER)

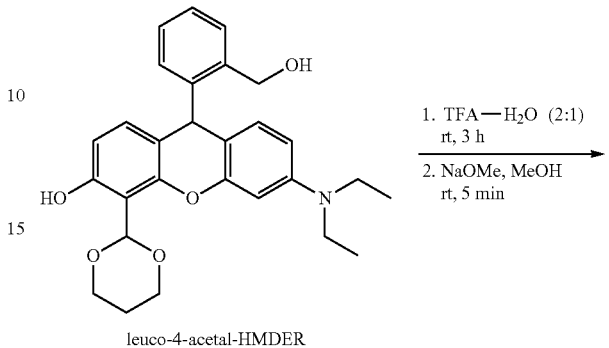

leuco-4-acetal-HMDER

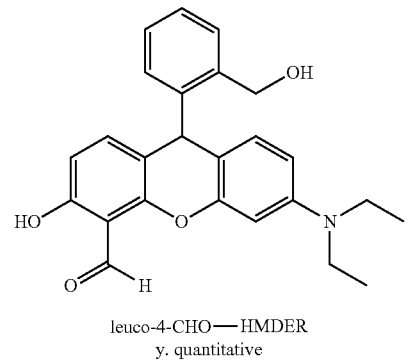

leuco-4-CHO—HMDER
y. quantitative

In an argon atmosphere, TFA-H$_2$O (2/1, 15 mL) was added to leuco-4-acetal-HMDER (151 mg/0.327 mmol) and the mixture was stirred for 3 hours at room temperature. The TFA and H$_2$O were removed by evaporation, CH$_2$Cl$_2$ and a 5% aqueous solution of K$_2$CO$_3$ were added, liquid separation was performed twice, and the organic phase was concentrated by evaporation. MeOH (5 mL) and NaOMe (18 mg, 0.333 mmol) were added to the resultant residue and the mixture was stirred for 5 minutes at room temperature. The solvent was removed by evaporation, CH$_2$Cl$_2$ and a saturated aqueous solution of NH$_4$Cl were added, liquid separation, was performed, and the organic phase was concentrated by evaporation. The resultant residue was purified by medium-pressure silica gel column chromatography (eluent: CH$_2$Cl$_2$/MeOH=98/2), and the desired compound leuco-4-CHO-HMDER was obtained as a pale pink solid (134 mg with a quantitative yield).

$^1$H NMR (CDCl$_3$): δ. 11.85 (s, 1H), 10.62 (s, 1H), 7.41-7.39 (m, 1H), 7.25-7.23 (m, 2H), 7.17-7.15 (m, 1H), 7.06 (d, 1H, J=8.7 Hz), 6.71 (d, 1H, J=8.7 Hz), 6.48 (d, 1H, J=8.7 Hz), 6.39 (d, 1H, J=2.6 Hz), 6.33 (dd, 1H, J=2.6 and 8.7 Hz), 5.40 (s, 1H), 4.74-4.61 (m, 2H), 3.33 (q, 4H, J=7.1 Hz), 1.16 (t, 6H, J=7.1 Hz). $^{13}$C NMR (CDCl$_3$): δ. 194.1, 162.2, 152.7, 150.5, 148.1, 144.5, 139.1, 138.1, 131.4, 130.2, 129.3, 128.7, 127.3, 115.3, 111.9, 110.4, 109.4, 108.7, 98.7, 63.3, 44.5, 38.8, 12.7. HRMS-ESI (m/z): [H+Na]$^+$ calculated for 426.1676 (C$_{25}$H$_{25}$NNaO$_4$), found 426.1670.

(Synthesis Example 8) Synthesis of (2S,3R,4S,5R,6R)-2-((3'-(diethyiamino)-5'-(difluoromethyl)-3H-spiro[isobenzofuran-1,9'-xanthen]-6'-yl)-oxy)-6-(hydroxymethyl)tetrahydro-2H-pyran-3,4,5-triol(4-CHF$_2$-HMDER-βGal)

was obtained. In an argon atmosphere, anhydrous CH$_2$Cl$_2$ (5 mL) and DAST (200 μL, 244 mg, 1.51 mmol) were added, and the mixture was stirred for 4 hours at room temperature. MeOH (10 mL) was added under ice cooling to quench the reaction, and the solvent was removed by evaporation. MeOH (40 mL) and NaOMe (600 mg, 11.1 mmol) were added to the resultant residue, the mixture was stirred for 1

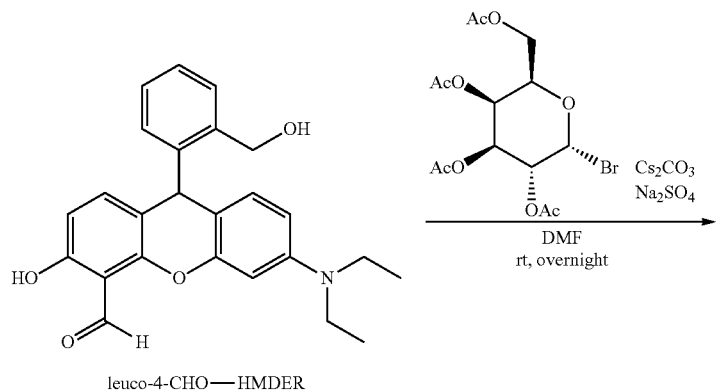

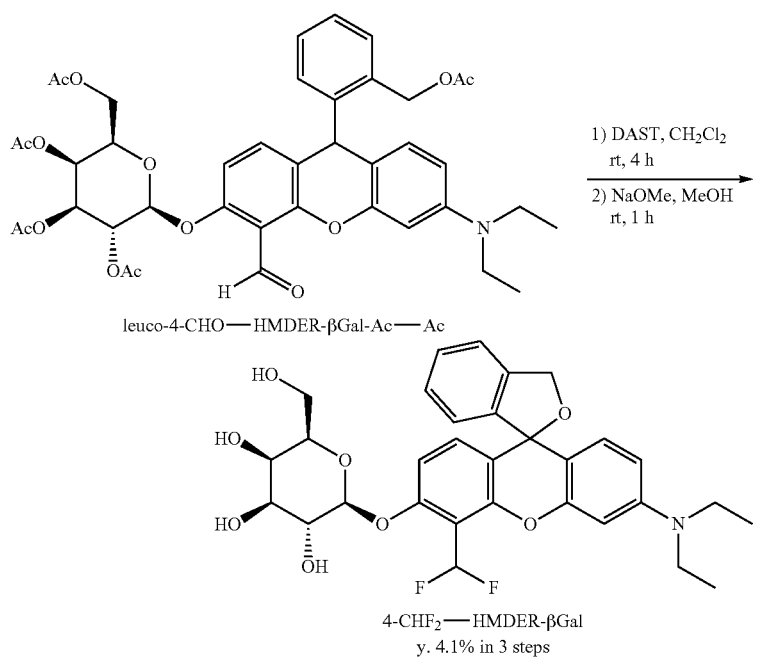

In an argon atmosphere, anhydrous DMF (3 mL), 2,3,4,6-tetra-O-acetyl-α-D-galactopyranosyl bromide (705 mg, 1.71 mmol), Cs$_2$CO$_3$ (970 mg, 2.98 mmol), and Na$_2$SO$_4$ (390 mg, 2.75 mmol), were added to leuco-4-CHO-HMDER (134 mg, 0.332 mmol) and the mixture was stirred overnight at room temperature. The solvent was removed by evaporation, CH$_2$Cl$_2$ and a saturated aqueous solution of NH$_4$Cl were added and liquid separation was performed three times, Na$_2$SO$_4$ was added to the organic phase, the product was dried and celite filtered, and the filtrate was concentrated by evaporation. The resultant residue was purified by medium-pressure silica gel column chromatography (eluent: CH$_2$Cl$_2$/EtOAc=98/2), and leuco-4-CHO-HMDER-βGal-Ac—Ac hour at room temperature, and the solvent was removed by evaporation. A saturated aqueous solution of NH$_4$Cl was added to the residue to neutralize the product, CH$_2$Cl$_2$ was added, and liquid separation was performed three times. Na$_2$SO$_4$ was added to the organic phase and drying was performed, celite filtration was performed, the filtrate was concentrated by evaporation, the resultant residue was purified by PLC (eluent: CH$_2$Cl$_2$/MeOH=9/1) and HPLC (A/B=50/50), and the desired compound 4-CHF$_2$-HMDER-βGal was obtained as a pale pink solid (8.0 mg with a yield of 4.1% in three steps).

$^1$H NMR (CD$_3$CN): δ. 7.45 (t, 1H, J=53.7 Hz), 7.42 (d, 1H, J=7.6 Hz), 7.40-7.36 (m, 1H), 7.28-7.24 (m, 1H), 7.06-7.03 (m, 1H), 6.92 (d, 1H, J=8.9 Hz), 6.83 (d, 0.5H, J=7.6 Hz), 6.83 (d, 0.5H, J=7.6 Hz), 6.74 (d, 0.5H, J=8.8 Hz), 6.73 (d, 0.5H, J=8.8 Hz), 6.48 (dd, 1H, J=2.6 and 8.8 Hz), 6.44 (d, 1H, J=2.6 Hz), 4.88 (dd, 1H, J=7.7 and 12.9 Hz), 3.83 (d, 1H, J=3.1 Hz), 3.72-3.58 (m, 4H), 3.53-3.48 (m, 1H), 3.37 (q, 4H, J=7.0 Hz), 1.13 (t, 6H, J=7.0 Hz). $^{13}$C NMR (100 MHz, CD$_3$CN): δ. 157.1, 151.9, 151.9, 150.5, 149.9, 146.3, 146.2, 140.2, 140.2, 133.8, 133.8, 130.4, 129.3, 129.2, 129.1, 124.2, 122.1, 121.7, 112.7 (t, J=233.5 Hz), 112.1, 111.8, 111.7, 110.7 (t, J=22.0 Hz), 110.6 (t, J=22.0 Hz), 109.8, 102.5, 102.4, 98.1, 03.9, 83.9, 76.5, 76.5, 74.1, 74.1, 72.9, 71.9, 71.9, 69.7, 62.2, 62.2, 45.0, 12.8. HRMS-ESI (m/z): [M+Na]$^+$ calculated for 608.2066 (C$_{31}$H$_{33}$F$_2$NNaO$_8$), found 608.2064.

(Synthesis Example 9) Synthesis of (2S,3R,4S,5R, 6R)-2-((3'-diethylamino)-5'-(fluoromethyl)-3H-spiro [isobenzofuran-1,9'-xanthen]-61'-yl)oxy)-6-(hydroxymethyl)tetrahydro-2H-pyran-3,4,5-triol(4-CHF$_2$-HMDER-βGal)

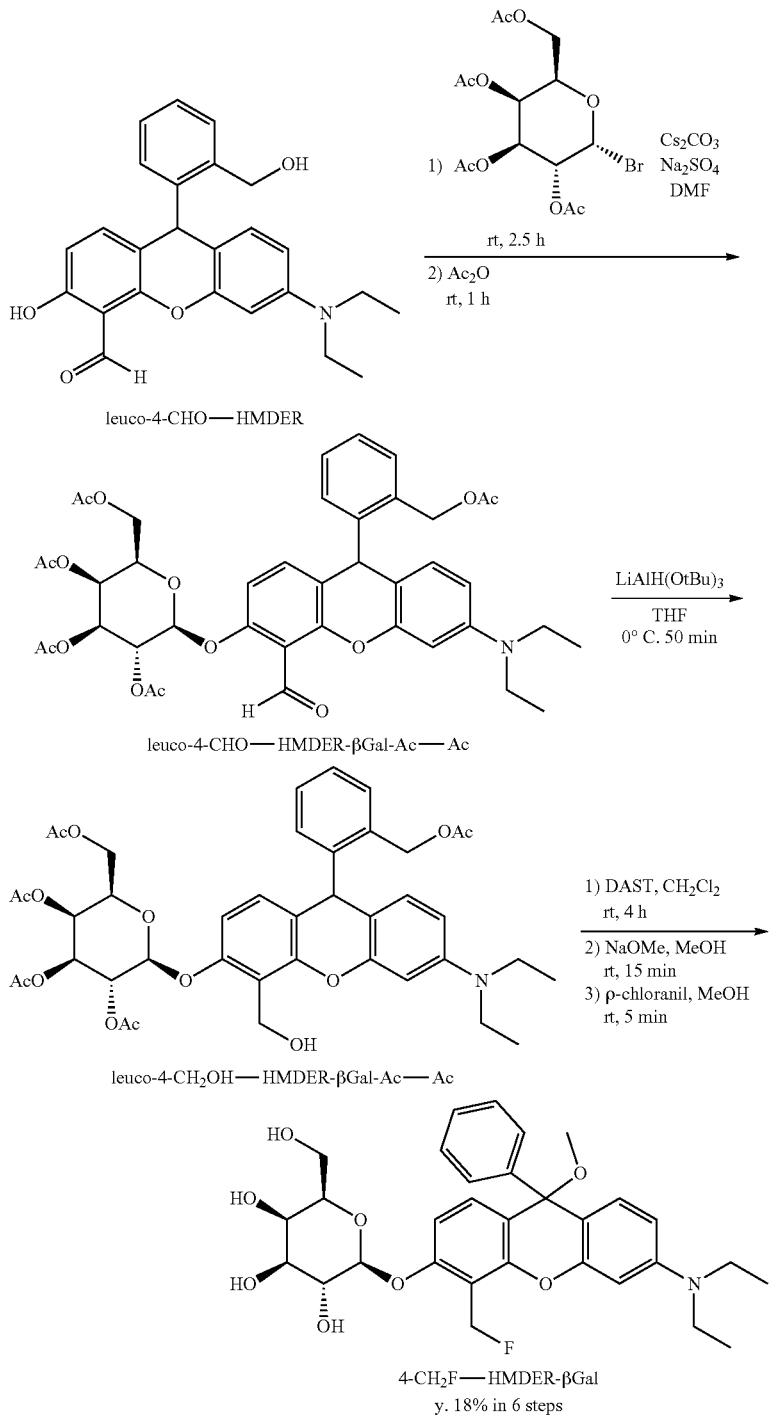

In an argon atmosphere, anhydrous DMF (6 mL), 2,3,4,6-tetra-O-acetyl-α-D-galactopyranosyl bromide (550 mg, 1.34 mmol), $Cs_2CO_3$ (1.50 g, 4.60 mmol), and $Na_2SO_4$ (400 mg, 2.82 mmol), were added to leuco-4-CHO-HMDER (249 mg, 0.616 mmol) and the mixture was stirred for 2 hours at room temperature. $Ac_2O$ (100 μL, 108 mg, 1.06 mmol) was added to the reaction liquid, and the mixture was further stirred for 1 hour at room temperature. The solvent was removed by evaporation, $CH_2Cl_2$ and a saturated aqueous solution of $NH_4Cl$ were added, liquid separation was performed three times, $Na_2SO_4$ was added to the organic phase, drying was performed, celite filtration was performed, and the filtrate was concentrated by evaporation. The resultant residue was purified by medium-pressure silica gel column chromatography (eluent: $CH_2Cl_2$/EtOAc=98/2), and leuco-4-CHO-HMDER-βGal-Ac—Ac was obtained. In an argon atmosphere, anhydrous THF (5 mL) and 1.0 M $LiAlH(OtBu)_3$ in THF (1 mL, 1.00 mmol) were added, the mixture was stirred for 50 minutes at 0° C., and a saturated aqueous solution of $NH_4Cl$ (3 mL) was added under ice cooling to quench the reaction. EtOAc (7 mL) was added and the mixture was stirred for 1 hour at room temperature, and the organic phase was extracted. $CH_2Cl_2$ and a saturated aqueous solution of Rochelle salt were added to the water phase and the mixture was stirred, and the operation for extracting the organic phase was performed twice. The organic phase was combined and concentrated by evaporation, the resultant residue was purified by medium-pressure silica gel column chromatography (eluent: $CH_2Cl_2$/EtOAc=98/2), and leuco-4-$CH_2OH$-HMDER-βGal-Ac—Ac was obtained. In an argon atmosphere, anhydrous $CH_2Cl_2$ (5 mL) and DAST (200 μL, 244 mg, 1.51 mmol) were added, the mixture was stirred for 30 minutes at room temperature, and MeOH (10 mL) was added under ice cooling to quench the reaction. The solvent was removed by evaporation, MeOH (20 mL) and NaOMe (700 mg, 13.0 mmol) were added to the resultant residue, the mixture was stirred for 5 minutes at room temperature, and a saturated aqueous solution of $NH_4Cl$ (2 mL) was added to quench the reaction. After concentration by evaporation, $CH_2Cl_2$ and a saturated aqueous solution of $NaHCO_3$ were added, and liquid separation was performed three times. $CH_2Cl_2$ was added to the water phase and liquid separation was performed, and the organic phase was combined. $Na_2SO_4$ was added to the organic phase and drying was performed, celite filtration was performed, and the filtrate was concentrated by evaporation. MeOH (10 mL) and p-chloranil (80 mg, 0.325 mmol) were added to the resultant residue and the mixture was stirred for 5 minutes at room temperature. The solvent was removed by evaporation, $CH_2Cl_2$ and a saturated aqueous solution of $NaHCO_3$ were added, liquid separation was performed three times, a saturated aqueous solution of NaCl was added to the organic phase, and the product was washed. The organic phase was celite filtered, and the filtrate was concentrated by evaporation. The resultant residue was purified by medium-pressure silica gel column chromatography (eluent: $CH_2Cl_2$/MeOH=98/2 to 94/6) and HPLC (A/B=50/50), and the desired compound 4-$CH_2F$-HMDER-βGal was obtained as a pale pink solid (65.9 mg with a yield of 18% in six steps).

$^1H$ NMR (400 MHz, $CD_3CN$): δ. 7.42 (d, 1H, J=7.6 Hz), 7.37 (t, 1H, J=7.4 Hz), 7.26 (t, 1H, J=7.5 Hz), 6.97 (d, 0.5H, J=8.9 Hz), 6.97 (d, 0.5H, J=8.9 Hz), 6.90 (d, 0.5H, J=8.9 Hz), 6.89 (d, 0.5H, J=8.9 Hz), 6.82 (d, 0.5H, J=7.6 Hz), 6.81 (d, 0.5H, J=7.6 Hz), 6.74 (d, 0.5H, J=8.8 Hz), 6.73 (d, 0.5H, J=8.8 Hz), 6.52 (d, 1H, J=2.5 Hz), 6.47 (dd, 1H, J=2.5 and 8.8 Hz), 5.81 (d, 2H, J=48.1 Hz), 5.25 (s, 2H), 4.86 (dd, 1H, J=7.7 and 12.8 Hz), 3.83 (d, 1H, J=3.2 Hz), 3.74-3.48 (m, 5H), 3.38 (q, 4H, J=7.0 Hz), 1.14 (t, 6H, J=7.0 Hz). $^{13}C$ NMR (100 MHz, $CD_3CN$): δ. 157.8, 157.7, 152.3, 152.2, 151.0, 149.8, 146.5, 146.3, 140.3, 140.2, 132.4 (d, J=4.6 Hz), 132.3 (d, J=4.7 Hz), 130.4, 129.2, 129.0, 124.2, 122.0, 121.1, 121.0, 113.0 (d, J=15.1 Hz), 113.0 (d, J=15.2 Hz), 112.4, 112.3, 111.5 (d, J=8.6 Hz), 111.5 (d, J=8.4 Hz), 109.6, 102.4, 102.3, 98.2, 98.2, 84.3, 84.2, 76.4, 76.3, 74.5 (d, J=158.7 Hz), 74.2, 72.3, 72.7, 72.0, 72.0, 69.7, 62.2, 62.2, 45.0, 12.8. HRMS-ESI (m/z): $[M+H]^+$ calculated for 568.2341 ($C_{31}H_{35}FNO_8$), found 568.2343.

It was confirmed from the test examples described below that the enzyme-specific retainable fluorescent compound of the present invention has excellent properties as a fluorescence imaging probe.

Test Example 1

Enzyme-Reaction-Specific Fluorescence Emission with β-Galactosidase

Emission of fluorescence by 2-$CHF_2$-HMDER-βGal, 4-$CHF_2$-HMDER-βGal, and 4-$CH_2F$-HMDER-βGal specifically in response to enzyme treatment by β-galactosidase was confirmed.

(Materials and Methods)

Absorption spectrum variation and fluorescence spectrum variation (excitation wavelength: 550 nm) caused by enzyme reaction of β-galactosidase and the enzyme-specific retainable fluorescent compound of the present invention 2-$CHF_2$-HMDER-βGal, 4-$CHF_2$-HMDER-βGal, or 4-$CH_2F$-HMDER-βGal for 30 minutes was measured in the presence of a 250 mM sodium phosphate buffer solution (pH: 7.4). Measurement was performed using a Shimadzu UV-2450 (manufactured by Shimadzu Corporation) and a Hitachi F-7000 (manufactured by Hitachi, Ltd.).

(Results)

Figure 1:
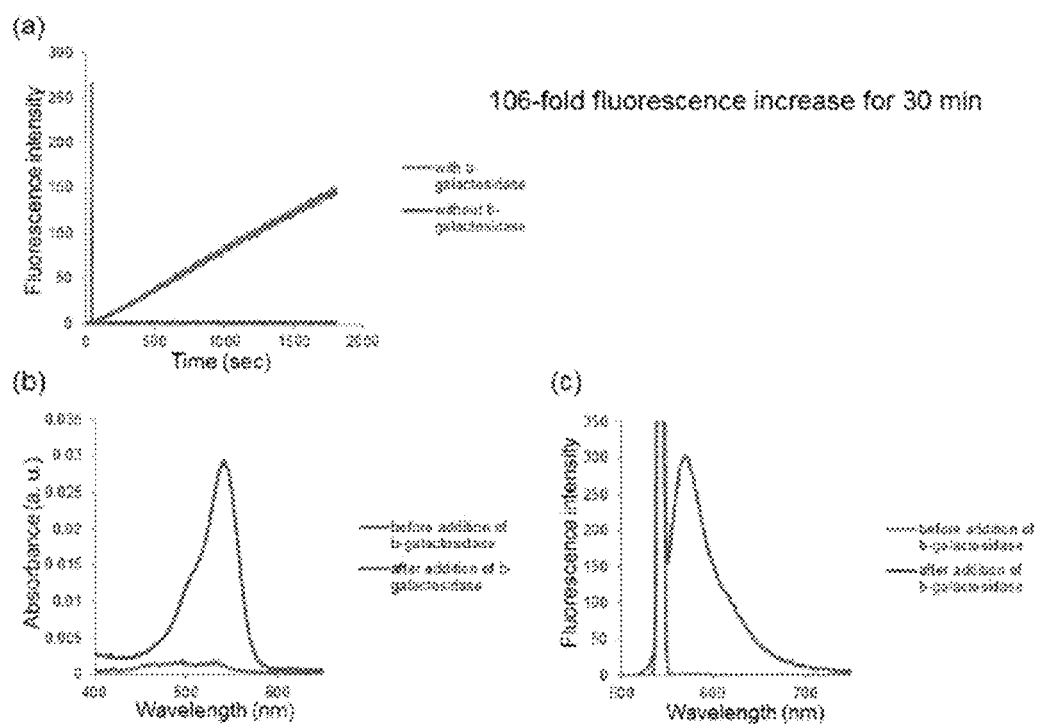
FIG. 1 A graph indicating the intensity (a), variation in absorption spectrum (b), and fluorescence spectrum (c) of fluorescence generated by enzyme reaction of the enzyme-specific retainable fluorescent, compound of the present invention 2-CHF$_2$-HMDER-βGal and β-galactosidase.
Figure 2:
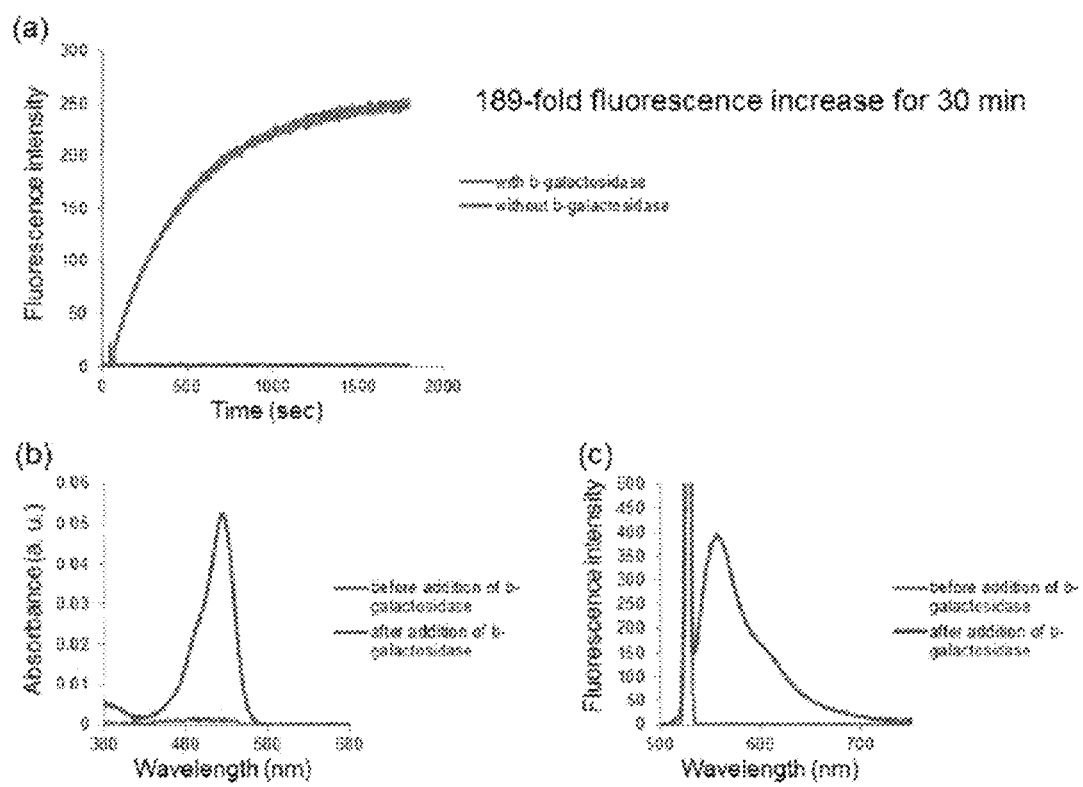
FIG. 2 A graph indicating the intensity (a), variation in absorption spectrum (b), and fluorescence spectrum (c) of fluorescence generated by enzyme reaction of the enzyme-specific retainable fluorescent compound of the present invention 4-CHF$_2$-HMDER-βGal and β-galactosidase.
Figure 3:
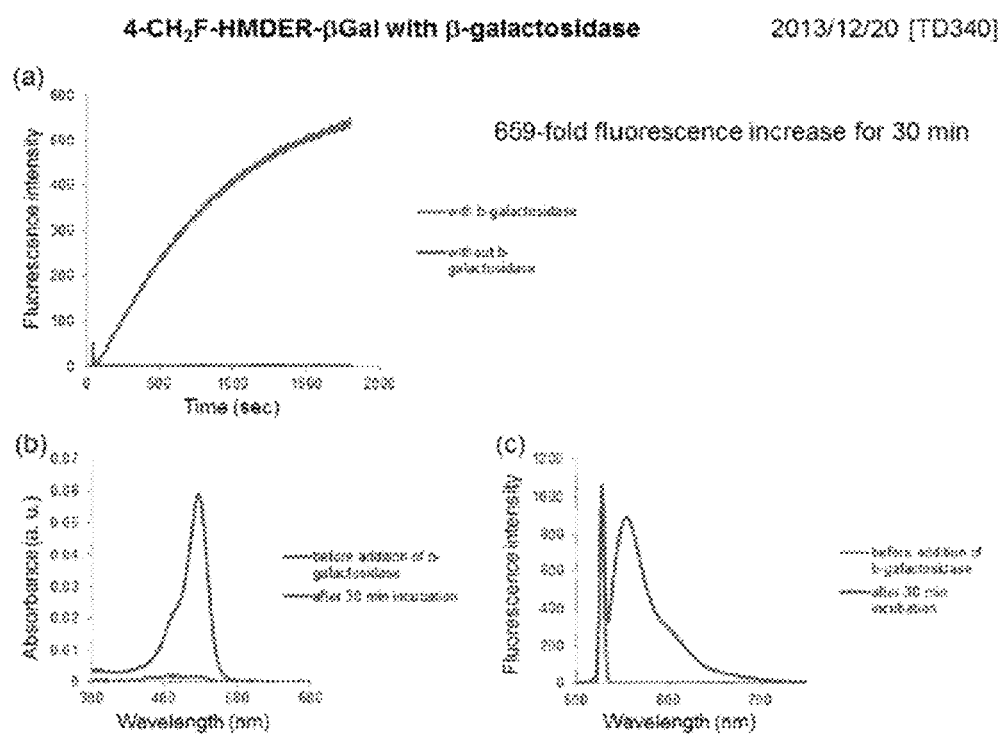
FIG. 3 A graph indicating the intensity (a), variation in absorption spectrum (b), and fluorescence spectrum (c) of fluorescence generated by enzyme reaction of the enzyme-specific retainable fluorescent compound of the present invention 4-CH$_2$F-HMDER-βGal and β-galactosidase.

2-$CHF_2$-HMDER-βGal, 4-$CHF_2$-HMDER-βGal, and 4-$CH_2F$-HMDER-βGal emitted fluorescence as a result of enzyme reaction with β-galactosidase (see FIGS. 1 through 3).

These results indicated that 2-$CHF_2$-HMDER-βGal, 4-$CHF_2$-HMDER-βGal, and 4-$CH_2F$-HMDER-βGal emit fluorescence specifically in response to enzyme activity of β-galactosidase.

Test Example 2

Binding of Fluorescent Dye to Coexisting Protein by β-Galactosidase Enzyme Reaction Using 2-$CHF_2$-HMDER-βGal, 4-$CHF_2$-HMDER-βGal, and 4-$CH_2F$-HMDER-βGal, it was confirmed that these compounds cleaved by β-galactosidase fluorescently label bovine serum albumin (BSA) protein coexisting therewith in solution.

(Materials and Methods)

(1) 2.5 μM 4-$CH_2F$-HMDER-βGal and 0.5 mg/mL BSA, (2) 2.5 μM 4-$CH_2F$-HMDER-βGal, 0.5 mg/mL BSA, and 5 U of β-galactosidase, (3) 2.5 μM 4-$CHF_2$-HMDER-βGal, 0.5 mg/mL BSA, and 5 U of β-galactosidase, (4) 2.5 μM 2-$CHF_2$-HMDER-βGal, 0.5 mg/mL BSA, and 5 U of β-galactosidase, and (5) 2.5 μM HMDER-βGal, 0.5 mg/mL BSA, and 5 U of β-galactosidase were each reacted in aqueous solution (500 mM sodium phosphate buffer solution having a pH of 7.4), after which the reaction products were subjected to SDS-PAGE (running gel: 10%, stacking gel: 4%, electrophoresis voltage: 200 V). Each gel obtained by SDS-PAGE was illuminated with excitation light having a wavelength of 488 nm, and fluorescence in the 540 to 600 nm range was observed at a PMT voltage of 1000 V (FIG. 4(a)). After observation, each gel was Coomassie stained and the position of the BSA on the gel was confirmed (FIG. 4(b)).

(Results)

Figure 4:
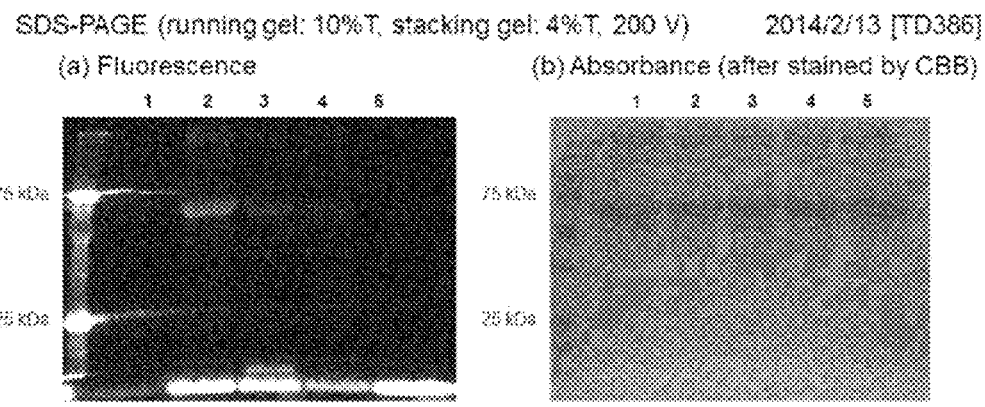
FIG. 4 A view indicating that a protein BSA coexisting in solution can be fluorescently labeled by enzyme reaction of the enzyme-specific retainable fluorescent compound of the present invention 2-CHF$_2$-HMDER-βGal, 4-CHF$_2$-HMDER-βGal, and 4-CH$_2$F-HMDER-βGal with β-galactosidase. (a) A fluorescence image obtained when an SDS-PAGE gel is excited by excitation light having a wavelength of 488 nm. Lane 1: 2.5 μM 4-CH$_2$F-HMDER-βGal and 0.5 mg/mL BSA; lane 2: 2.5 μM 4-CH$_2$F-HMDER-βGal, 0.5 mg/mL BSA, and 5 U of β-galactosidase; lane 3: 2.5 μM 4-CH$_2$F-HMDER-βGal, 0.5 mg/mL BSA, and 3 U of β-galactosidase; lane 4: 2.5 μM 2-CHF$_2$-HMDER-βGal, 0.5 mg/mL BSA, and 5 U of β-galactosidase; lane 5: 2.5 μM HMDER-βGal, 0.5 mg/mL BSA, and 5 U of β-galactosidase. (b) View of the abovementioned SDS-PAGE gel when Coomassie stained.

Fluorescence was observed at the band of BSA after SDS PAGE by reacting 2-CHF$_2$-HMDER-βGal, 4-CHF$_2$-HMDER-βGal, or 4-CH$_2$F-HMDER-βGal with β-galactosidase in the presence of BSA (see the bands near 75 kDa in lanes 2 through 4 of FIG. 4). Fluorescence was not observed in the sample not including β-galactosidase (lane 1 of FIG. 4) or the sample in which HMDER-βGal was used (lane 5 of FIG. 4).

The above results suggest that 2-CHF$_2$-HMDER-βGal, 4-CHF$_2$-HMDER-βGal, and 4-CH$_2$F-HMDER-βGal change in response specifically to β-galactosidase activity and thereby covalently bond to BSA, and the above results demonstrate that a protein coexisting in solution can be fluorescently labeled in enzyme-activity-specific fashion through use of the enzyme-specific retainable fluorescent compound of the present invention.

Test Example 3

Binding of Fluorescent Dye to Intracellular Protein by β-Galactosidase Enzyme Reaction Enzyme-activity-specific fluorescent labeling of an intracellular protein by 2-CHF$_2$-HMDER-βGal, 4-CHF$_2$-HMDER-βGal, and 4-CH$_2$F-HMDER-βGal was confirmed.

(Materials and Methods)

HEK cells (HEK-lacZ cells) expressing β-galactosidase and HEK cells were used.

(1) 2.5 μM 4-CH$_2$F-HMDER-βGal and 20 μL of 1.5 mg/mL HEK cell lysate, (2) 2.5 μM 4-CH$_2$F-HMDER-βGal and 20 μL of 1.5 mg/mL HEK-lacZ cell lysate, (3) 2.5 μM 4-CHF$_2$-HMDER-βGal and 20 μL of 1.5 mg/mL HEX-lacZ cell lysate, (4) 2.5 μM 2-CHF$_2$-HMDER-βGal and 20 μL of 1.5 mg/mL HEK-lacZ cell lysate, and (5) 2.5 μM HMDER-βGal and 20 μL of 1.5 mg/mL HEK-lacZ cell lysate were each incubated for 30 minutes at 37° C. in the presence of 5% CO$_2$, after which the reaction products were subjected to SDS-PAGE (running gel: 10%, stacking gel: 4%, electrophoresis voltage: 200 V). Each gel obtained by SDS-PAGE was irradiated with excitation light having a wavelength of 488 nm, and fluorescence in the 540 to 600 nm range was observed at a PMT voltage of 1000 V (FIG. 5(a)). After observation, each gel was Coomassie stained and the position of the BSA on the gel was confirmed (FIG. 5(b)).

(Results)

Figure 5:
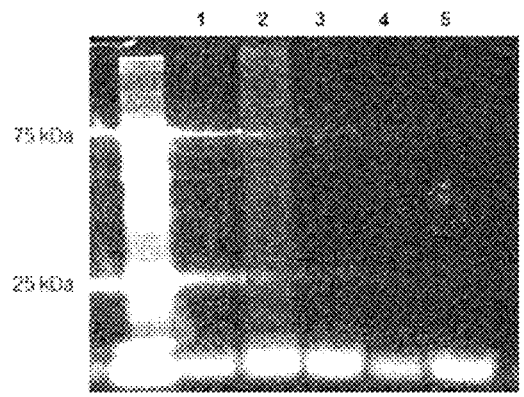
FIG. 5 A view indicating that the enzyme-specific retainable fluorescent compound of the present invention 2-CHF$_2$-HMDER-βGal, 4-CHF$_2$-HMDER-βGal, and 4-CH$_2$F-HMDER-βGal fluorescently labels an intracellular protein in enzyme-activity-specific fashion. (a) A fluorescence image obtained when an SDS-PAGE gel is excited by excitation light having a wavelength of 486 nm. Lane 1: 2.5 μM 4-CH$_2$F-HMDER-βGal and 20 μL of 1.5 mg/mL HEK cell lysate; lane 2: 2.5 μM 4-CH$_2$F-HMDER-βGal and 20 μL of 1.5 mg/mL HEK-lacZ cell lysate; lane 3: 2.5 μM 4-CHF$_2$-HMDER-βGal and 20 μL of 1.5 mg/mL HEK-lacZ cell lysate; lane 4: 2.5 μM 2-CHF$_2$-HMDER-βGal and 20 μL of 1.5 mg/mL HEK-lacZ cell lysate; lane 5: 2.5 μM HMDER-βGal and 20 μL of 1.5 mg/mL HEK-lacZ cell lysate. (b) View of the abovementioned SDS-PAGE gel when Coomassie stained.
Figure 5:
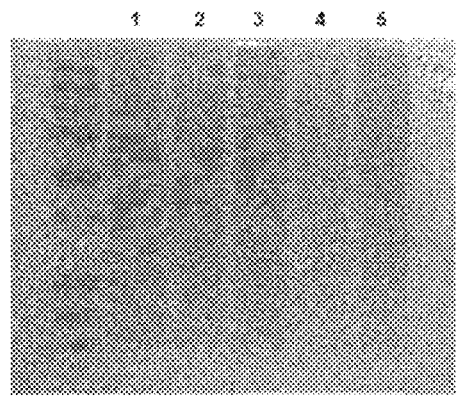

Fluorescence labeling to the intracellular protein was confirmed in the samples in which 2-CHF$_2$-HMDER-βGal, 4-CHF$_2$-HMDER-βGal, and 4-CH$_2$F-HMDER-βGal were incubated with HEK-lacZ cells (lanes 2 through A of FIG. 5). Fluorescence was not confirmed in the sample in which HEK cells not expressing β-galactosidase were used (lane 1 of FIG. 5), or in the sample in which HMDER-βGal was used (lane 5 of FIG. 5).

The above results suggest that 2-CHF$_2$-HMDER-βGal, 4-CHF$_2$-HMDER-βGal, and 4-CH$_2$F-HMDER-βGal change in response specifically to β-galactosidase activity and thereby covalently bond to the intracellular protein, and the above results demonstrate that an intracellular protein can be fluorescently labeled in enzyme-activity-specific fashion through use oil the enzyme-specific retainable fluorescent compound of the present invention.

Test Example 4

Fluorescence Imaging of Living Cells Expressing β-Galactosidase

It was confirmed that the enzyme-specific retainable fluorescent compound of the present invention can be used for fluorescence imaging of a living lacZ-positive cell.

(Materials and Methods)

HEK cells, HEK-lacZ cells, and a mixture thereof were incubated (at 37° C. in the presence of 5% CO$_2$) for 30 minutes together with 1 μM 4-CH$_2$F-HMDER-βGal or HMDER-βGal, after which a fluorescence image and a differential interference image (DIC) of the cells were acquired using a confocal microscope, before and after washing twice with culture medium. Cells incubated with 4-CH$_2$-HMDER-βGal were fixed by treating with 4% PFA for 10 minutes at room temperature, and were observed in the same manner. A TCS SP5 X (manufactured by Leica) equipped with white light laser and an HCX PL APO CS 40x/1.25 objective lens (manufactured by Leica) was used as the confocal microscope, which was controlled by LAS AF software. The observation conditions were as follows: white light laser (WLL): 80% to 25%, excitation wavelength: 525 nm, observation wavelength: 535 to 595 nm, gain: 800 V (PMT1)/350 V (Scan-DIC), offset: 0%, pinhole: 67.88 μM (Airy disk).

(Results)

Figure 6:
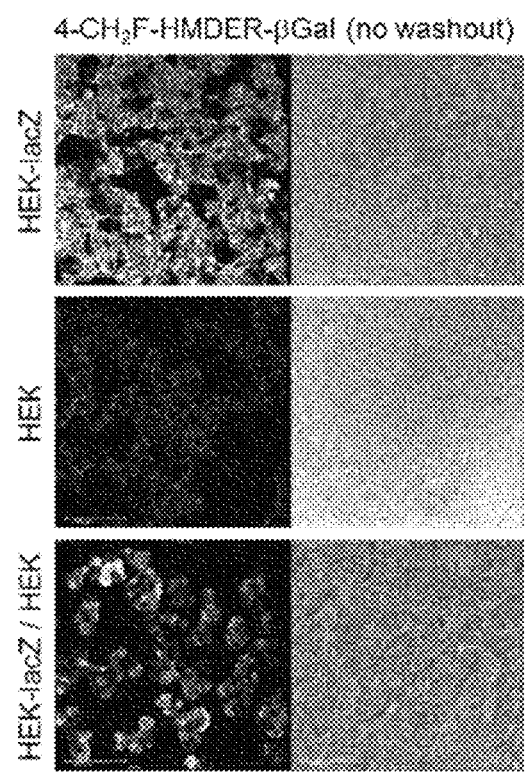
FIG. 6 View indicating that the enzyme-specific retainable fluorescent compound of the present invention 4-CH$_2$F-HMDER-βGal can be used for fluorescence imaging of living cells at a single-cell level.
Figure 6:

When cells were observed without being washed with culture medium after incubation with the test compound, the HEK-LacZ cells incubated with 4-CH$_2$F-HMDER-βGal exhibited clear fluorescence (left side of FIG. 6). In the mixture of HEK-LacZ cells and HEK cells, a definite difference in fluorescence level among individual cells was observed, indicating that detection/fluorescence imaging of β-galactosidase activity for each cell is possible. Meanwhile, fluorescence imaging of β-galactosidase activity of individual eels was not possible when HMDER-βGal was used (right side of FIG. 6).

Figure 7:
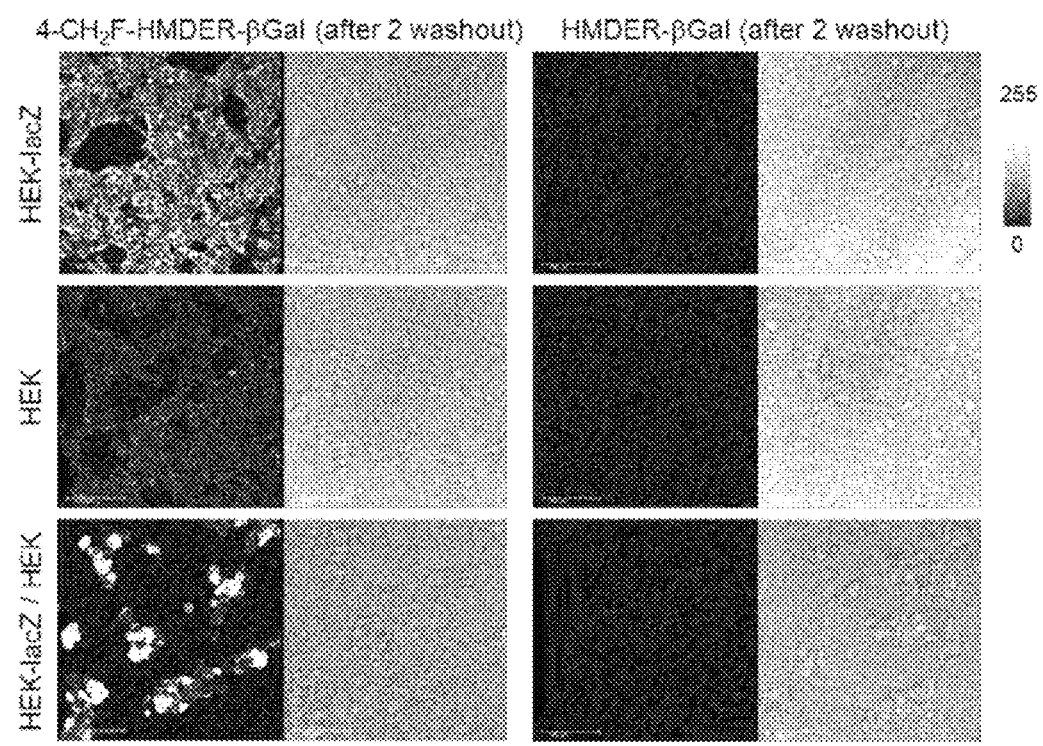
FIG. 7 A view indicating that the enzyme-specific retainable fluorescent compound of the present invention 4-CH$_2$F-HMDER-βGal has excellent retention in cells.

Also in the case in which cells were observed after being incubated with the test compound and subsequently washed twice with culture medium, there was almost no change in fluorescence intensity when 4-CH$_2$F-HMDER-βGal was used, indicating that there is almost no leakage from cells of fluorescent dye generated after the enzyme reaction of 4-CH$_2$F-HMDER-βGal and β-galactosidase (FIG. 7).

Figure 8:
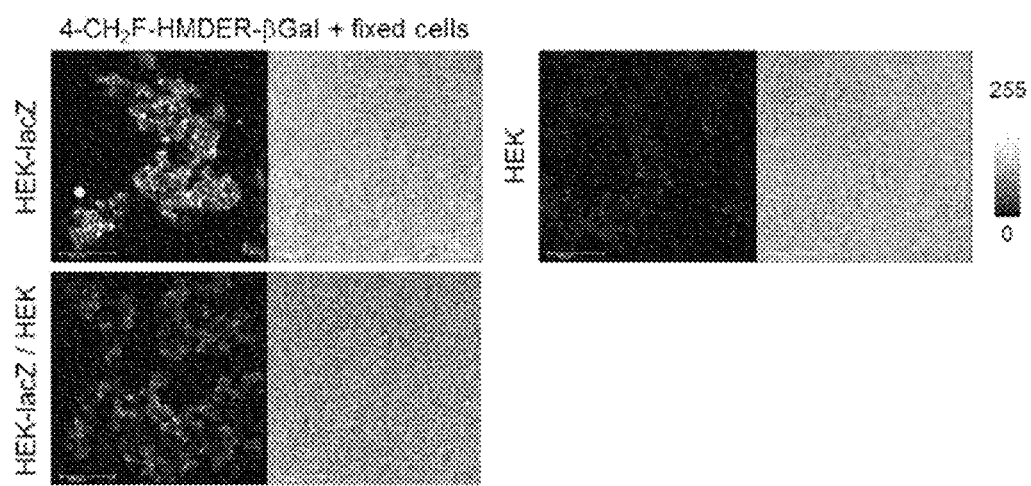
FIG. 8 View indicating that the same fluorescence imaging as is possible with living cells is possible for an immobilized sample, through use of the enzyme-specific retainable fluorescent compound of the present invention 4-CH$_2$F-HMDER-βGal.

Fluorescence imaging with the fixed samples was also possible by incubating with 4-CH$_2$F-HMDER-βGal, as in the case with living cells (FIG. 8).

The above results demonstrate that through use of the enzyme-specific retainable fluorescent compound of the present invention, live-cell fluorescence imaging in a single-cell resolution is possible, due to its excellent retention in cells, and there is almost no leakage of fluorescent dye from cells ever, after fixation.

Test Example 5

Detection of β-Galactosidase Activity in Living Cells Using Flow Cytometry

It was confirmed that enzyme activity in living cells can be detected using flow cytometry through use of the enzyme-specific retainable fluorescent compound of the present invention.

(Materials and Methods)

HEK cells, HEK-lacZ cells, and a mixture thereof were incubated with 1 μM 4-CH$_2$F-HMDER-βGal or HMDER-βGal at 37° C. in the presence of 5% CO$_2$ for 30 minutes.

These cells were analyzed by excitation light having a wavelength of 488 nm using an Accuri C6 (Accuri Cytometers, Inc.) flow cytometer.

(Results)

Figure 9:
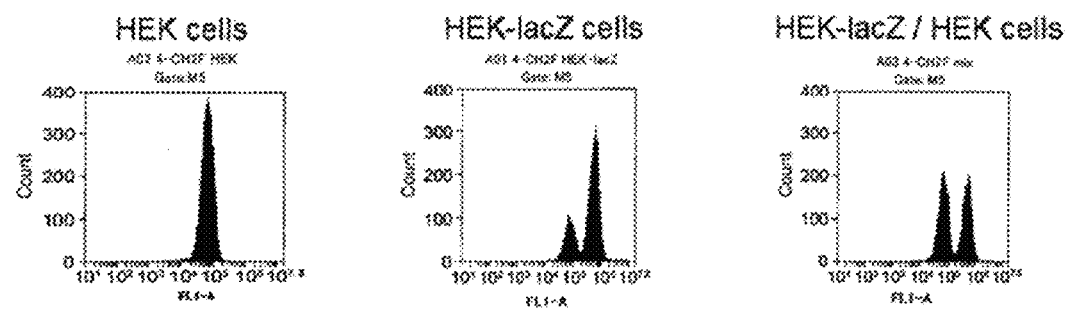
FIG. 9 View indicating that cells having different enzyme activity can be detected or differentiated using flow cytometry through use of the enzyme-specific retainable fluorescent compound of the present invention 4-CH$_2$F-HMDER-βGal. (a) Flow cytometry results for HEK cells, HEK-LacZ cells, and a mixture thereof reacted with 4-CH$_2$F-HMDER-βGal. (b) Flow cytometry results for HEK cells, HEK-LacZ cells, and a mixture thereof reacted with HMDER-βGal.
Figure 9:
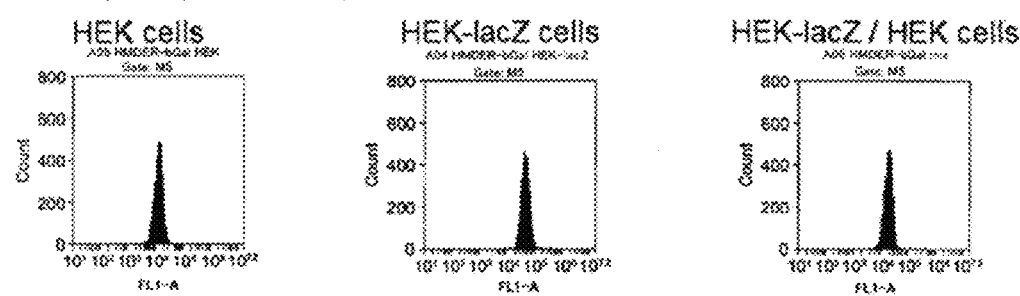

When the mixture of HEX-LacZ cells and HEK cells incubated with 4-CH$_2$F-HMDER-βGal was analyzed using flow cytometry, peaks corresponding to the HEK-LacZ cells and the HEK cells were distinctly observed, and it was possible to clearly differentiate between these cell types on the basis of the difference in fluorescence intensity thereof (FIG. 9(a)). Meanwhile, in the mixture of HEK-LacZ cells and HEK cells incubated with HMDER-βGal, the cells could not be differentiated on the basis of the results of flow cytometry (FIG. 9(b)).

The above results demonstrate that through use of the enzyme-specific retainable fluorescent compound of the present invention, cells having different enzyme activity can be distinctly detected and differentiated using flow cytometry.

Test Example 6

Fluorescence Imaging of Non-Fixed Biological Tissue Having β-Galactosidase Activity It was confirmed that the enzyme-specific retainable fluorescent compound of the present invention can be applied to fluorescence imaging of a living biological tissue.

(Materials and Methods)

Wing primordia (wing discs) of a (en-lacZ) fruit fly (*Drosophila melanogaster*) expressing β-galactosidase were incubated with 20 μM 4-CH$_2$F-HMDER-βGal or HMDER-βGal for 30 minutes at room temperature, and then observed under a confocal microscope (TCS SP5, manufactured by Leica, controlled by LAS AF software). The observation conditions were as follows: Ar: 40% to 25%, excitation light: 314 nm, emission wavelength: 535 to 595 nm (HyD2), 20× magnification.

(Results)

Figure 10:
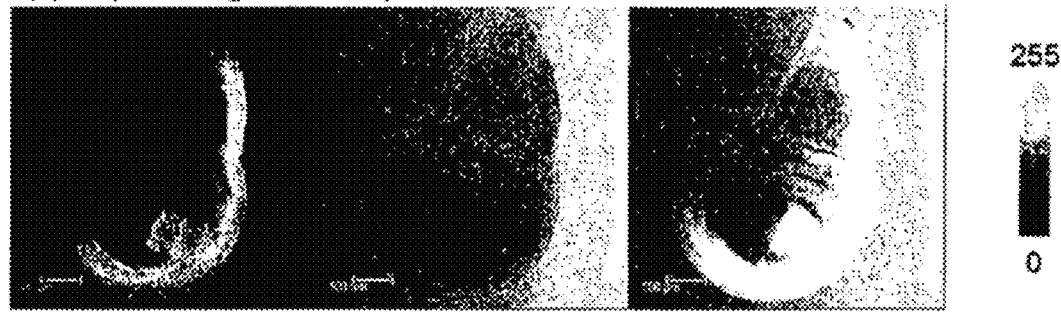
FIG. 10 A view indicating that the enzyme-specific retainable fluorescent compound of the present invention 4-CH$_2$F-
Figure 10:
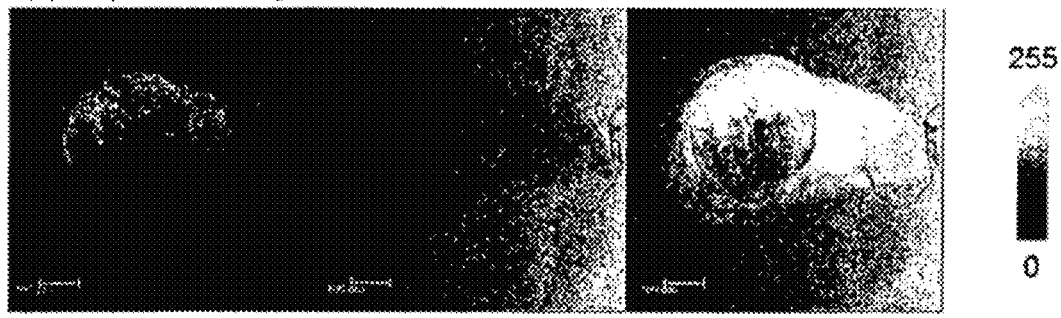

When fluorescence imaging vas performed using 4-CH$_2$F-HMDER-βGal, because the fluorescent dye formed as the enzyme reaction product does not diffuse, selective fluorescence imaging of the region of interest (posterior section) having β-galactosidase activity was possible (FIG. 10(a)). Meanwhile, when fluorescence imaging was performed using HMDER-βGal, the fluorescent dye formed as the enzyme reaction product diffused over time, and the region of interest having β-galactosidase activity could not be discerned (FIG. 10(b)).

The above results demonstrate that through use of the enzyme-specific retainable fluorescent compound of the present invention, diffusion of the fluorescent dye is suppressed, and fluorescence imaging in a living biological tissue is possible.

Test Example 7

Fluorescence Imaging of Fixed Fly Intestinal Tract Expressing β-Galactosidase with Single-Cell Resolution It was confirmed that fluorescence imaging of cells of interest in a tissue with single-cell resolution is possible through use of the enzyme-specific retainable fluorescent compound of the present invention.

(Materials and Methods)

A fruit fly (esg-lacZ) expressing β-galactosidase in the midgut thereof was dissected and fixed with 4% FPA. Then, 4-CH$_2$F-HMDER-βGal was added and reacted for 10 minutes. After washed out and mounted in 80% glycerol, observation was performed using a fluorescence microscope (TCS SP5, manufactured by Leica, controlled by LAS AF software). Intestinal stem cells (esg-GFP) of *Drosophila* expressing GFP were observed as the control. The observation conditions were as follows: excitation light: 514 nm, observation wavelength: 535 to 595 nm (HyD2), 40× magnification.

(Results)

By reacting fruit fly (esg-LacZ) with 4-CH$_2$F-HMDER-βGal, it was possible to confirm a cell emitting fluorescence in a tissue (FIG. 11(a)). The image was similar to a fluorescence image (FIG. 11(b)) of *Drosophila* intestinal stem cells (esg-GFP).

The above results demonstrate that single-cell fluorescence imaging is possible through use of the enzyme-specific retainable fluorescent compound of the present invention. It was also confirmed that the same fluorescence imaging is possible also in intestinal tract cells expressing β-galactosidase which are not fixed.

Test Example 8

Ex Vivo Fluorescence Imaging of a Model Mouse Inoculated with Ovarian Cancer

It was confirmed that selective fluorescence imaging of a cancer site is possible through use of the enzyme-specific retainable fluorescent compound of the present invention.

(Materials and Methods)

A cancer model mouse inoculated with ovarian cancer cells SHIN3 was produced. Acidic β-galactosidase activity is known to be elevated in ovarian cancer cells. 4-CH$_2$F-HMDER-βGal was intraperitoneally administered to the cancer model mouse, and fluorescence was observed 1 hour later using a Maestro in-vivo imaging system (CRi). The observation conditions were as follows: excitation light: 490 to 530 nm, observation wavelength: 550 to 800 nm.

(Results)

As a result of fluorescence observation, fluorescence originating from the fluorescent dye generated after enzyme reaction was observed from regions (indicated by a white arrow) thought to be cancer sites (FIG. 12). When the fluorescence was separated (unmixed) by fluorescence spectra, it was possible to separate the fluorescence at tumor from autofluorescence.

The above results demonstrate that selective fluorescence imaging of a cancer site in a living body is possible through use of the enzyme-specific retainable fluorescent compound of the present invention.

Test Example 9

Fluorescence Imaging of β-Galactosidase Activity Expressed in Mosaic Pattern in Non-Fixed Fruit Fly Tissue It was confirmed that fluorescence imaging of β-galactosidase-positive cells distributed in a mosaic pattern in a living biological tissue is possible through use of the enzyme-specific retainable fluorescent compound of the present invention.

(Materials and Methods)

A male His2Av-mRFP1, FRT80B/TM6B fruit fly (*Drosophila melanogaster*) and a female hs-flp; arm-lacZ FRT80B fruit fly were crossed, a heat shock at a temperature of 37° C. for 1 hour was applied to the offspring at the first-instar larval stage 30 hours after hatching thereof, and cells having the following three genotypes were expressed in the wing primordia (wing discs): (1) cells expressing only β-galactosidase (arm-lacZ), (2) cells expressing only red fluorescent protein (mRFP1) (His2Av-mRFP1), and (3) cells expressing both β-galactosidase and mRFP1 (arm-lacZ/His2Av-mRFP1). Wing primordia dissected from a third-instar (last instar) larva were immersed for 30 minutes in a culture medium including 10 μM 4-CH$_2$F-HMDER-βGal and observed under a confocal microscope (TCS SP5, manufactured by Leica, controlled by LAS AF software). The observation conditions were as follows: (4-CH$_2$F-HMDER-βGal) excitation light: 514 nm, observation wavelength: 525 to 585 nm, (mRFP1) excitation light: 594 nm, emission wavelength: 610 to 700 nm, 63× magnification.

(Results)

When fluorescence imaging was performed using 4-CH$_2$F-HMDER-βGal, the mosaic pattern of the cells having the three genotypes described above was clearly visualized (FIG. 13).

The above results demonstrate that cells expressing β-galactosidase which are present in a living biological tissue can be distinctly visualized/discerned through use of the enzyme-specific retainable fluorescent compound of the present invention.

Test Example 10

Fluorescence Imaging of Fly Fat Body Expressing β-Galactosidase Activity with Single-Cell Resolution It was confirmed that fluorescence imaging of β-galactosidase activity randomly expressed in a biological tissue is possible with single-cell resolution through use of the enzyme-specific retainable fluorescent compound of the present invention.

(Materials and Methods)

In order to analyze cells in fruit fly (Drosophila melanogaster) fat body, overexpression of β-galactosidase was induced by crossing UAS-lacZ with hs-flp$^{122}$; Actin>y>Gal4 using a flip-out technique. To perform living-cell fluorescence imaging, fat bodies were dissected from a third-instar (final instar) fly and incubated for 29 minutes in a culture medium including 10 μM 4-CH$_2$F-HMDER-βGal and 16 μM Hoechst 33342 (cell nuclear stain), and the fat bodies were washed with PBS and immersed in 80% glycerol. To perform immunostaining, the dissected adipocytes were immersed for 20 minutes in PBS containing 4% paraformaldehyde (PFA) and fixed. After blocking, the adipocytes were immersed for 30 minutes with primary antibodies (1:250, Promega Corporation) against β-galactosidase, 10 μM 4-CH$_2$F-HMDER-βGal, 16 μM Hoechst 33342, followed by incubation with Alexa 647-labelled secondary antibodies, and the fat bodies were observed under a confocal microscope (TCS SP5, manufactured by Leica, controlled by LAS AF software). The observation conditions were as follows: (Hoeschst 33342) excitation light: 405 nm, observation wavelength: 415 to 490 nm, (4-C$_2$F-HMDER-βGal) excitation light: 514 nm, observation wavelength: 525 to 600 nm, (Alexa 647 modified secondary antibodies) excitation light: 633 nm, observation wavelength: 640 to 700 nm, 40× magnification.

(Results)

Fluorescence imaging using 4-CH$_2$F-HMDER-βGal was performed, and it was confirmed that it is possible to perform fluorescent imaging of cells of interest in which β-galactosidase is expressed (FIG. 14).

The above results demonstrate that β-galactosidase-expressing cells which are randomly present in a biological tissue can be visualized/discerned with single-cell resolution, through use of the enzyme-specific retainable fluorescent compound of the present invention.

INDUSTRIAL APPLICABILITY

The present invention provides a fluorescent compound for emitting fluorescence in enzyme-activity-specific fashion while at the same time being retained in a living cell having the enzyme, whereby the cell can be selectively visualized with single-cell resolution both in living or fixed tissues. The present invention also provides a fluorescence imaging probe which uses the fluorescent compound, a detection method which uses the fluorescent probe, and a detection kit or detection agent. The enzyme-specific retainable fluorescent compound of the present invention and the imaging method using the same can be used as molecular tools for elucidating mechanisms of cell aging, and also have a wide range of applications in such fields as resting and diagnosis using a cancer-cell-specific fluorescence imaging probe.

The invention claimed is:

1. An enzyme-specific retainable fluorescent compound comprising a compound represented by Formula (I') below or a salt thereof

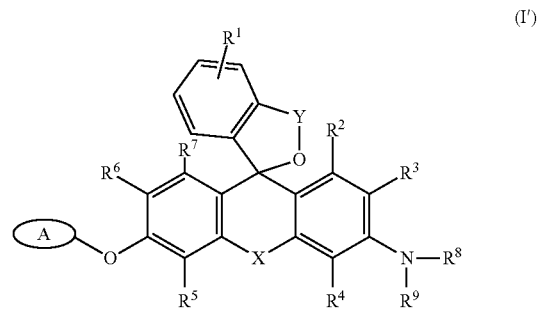

(I')

wherein, A representing a monovalent group which is cleaved by an enzyme; $R^1$ representing a hydrogen atom or one to four same or different substituents bonded to the benzene ring; $R^3$, $R^4$, $R^5$, and $R^6$ each independently representing —CFR$^{10}$R$^{11}$ or —CF$_2$R$^{12}$, or a hydrogen atom, a hydroxyl group, an alkyl group, or a halogen atom; $R^2$ and $R^7$ each independently representing a hydrogen atom, a hydroxyl group, an alkyl group, or a halogen atom; $R^8$ and $R^9$ each independently representing a hydrogen atom or an alkyl group; $R^{10}$, $R^{11}$, and $R^{12}$ each independently representing a hydrogen atom, an alkyl group, or an alkenyl group; X representing an oxygen atom, Se, CR$^{13}$R$^{14}$, or SiR$^{15}$R$^{16}$; $R^{13}$, $R^{14}$, $R^{15}$, and $R^{16}$ each independently representing a hydrogen atom or an alkyl group; Y representing a C$_{1-3}$ alkylene group; and at least one of $R^3$, $R^4$, $R^5$, and $R^6$ representing —CFR$^{10}$R$^{11}$ or —CF$_2$R$^{12}$.

2. The enzyme-specific retainable fluorescent compound according to claim 1, said enzyme being a hydrolase comprising a reporter enzyme.

3. The enzyme-specific retainable fluorescent compound according to claim 1, said enzyme being an enzyme expressed or activated specifically in a cancer cell.

4. The enzyme-specific retainable fluorescent compound according to claim 2, said reporter enzyme being β-galactosidase, and A being a galactopyranosyl group.

5. The enzyme-specific retainable fluorescent compound according to claim 1, at least one of $R^3$, $R^4$, $R^5$, and $R^6$ being —$CFR^{10}R^{11}$.

6. The enzyme-specific retainable fluorescent compound according to claim 1, at least one of $R^3$, $R^4$, $R^5$, and $R^6$ being —$CH_2F$.

7. An enzyme-specific retainable fluorescent compound comprising a compound represented by any one of Formulas (Ia) through (Ic) below or a salt thereof

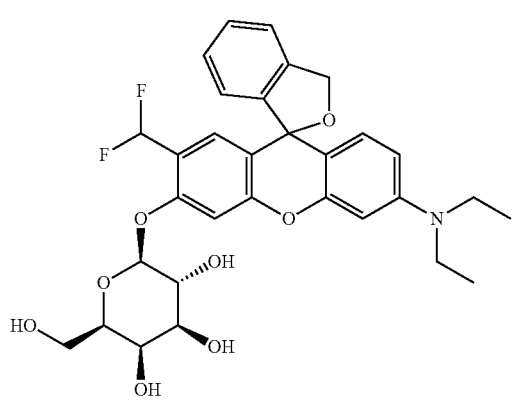

(Ia)

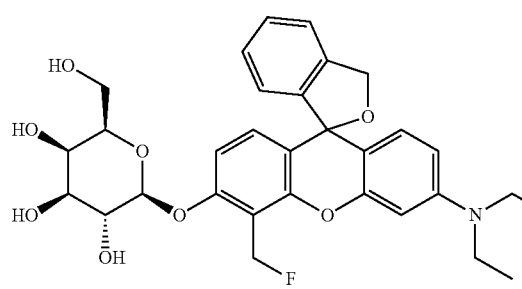

(Ib)

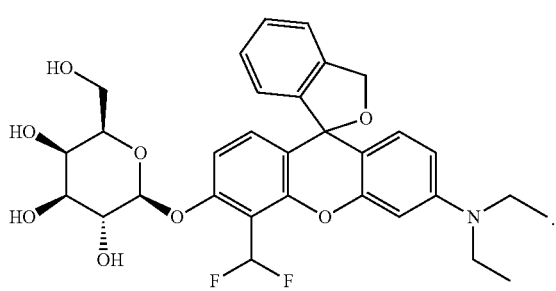

(Ic)

8. A fluorescence imaging probe containing the enzyme-specific retainable fluorescent compound according to claim 1.

9. A composition or kit for visualizing or detecting a target cell in which a specific enzyme is expressed, the composition or kit containing the enzyme-specific retainable fluorescent compound according to claim 1.

10. The composition or kit according to claim 9, said target cell being a cell expressing β-galactosidase.

11. The composition or kit according to claim 9, said target cell being a cancer cell.

12. A method for detecting a target cell in winch a specific enzyme is expressed, the method comprising the steps of:
bringing the enzyme-specific retainable fluorescent compound of claim 1 into contact ex vivo with the enzyme expressed in the target cell, and
inducing fluorescence by excitation light irradiation.

13. A method for detecting a target cell in which a specific enzyme is expressed, the method comprising bringing the enzyme-specific retainable fluorescent compound according to claim 1 into contact with an enzyme expressed specifically in a target cell at ex vivo.

14. The method according to claim 12, said target cell being a cell expressing β-galactosidase.

15. The method according to claim 12, said target cell being a cancer cell.

16. A compound represented by Formula (II) below

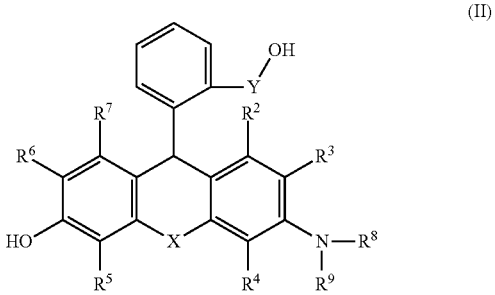

(II)

wherein, $R^3$, $R^4$, $R^5$, and $R^6$ each independently representing —C(=O)H, a hydrogen atom, a hydroxyl group, an alkyl group, or a halogen atom; $R^2$ and $R^7$ each independently representing a hydrogen atom, a hydroxyl group, an alkyl group, or a halogen atom; $R^8$ and $R^9$ each independently representing a hydrogen atom or an alkyl group; X representing an oxygen atom, Se, $CR^{13}R^{14}$, or $SiR^{15}R^{16}$; $R^{13}$, $R^{14}$, $R^{15}$, and $R^{16}$ each independently representing a hydrogen atom or an alkyl group; Y representing a $C_{1-3}$ alkylene group; and at least one of $R^3$, $R^4$, $R^5$, and $R^6$ representing —C(=O)H.

17. A compound represented by Formula (IIa) or (IIb)

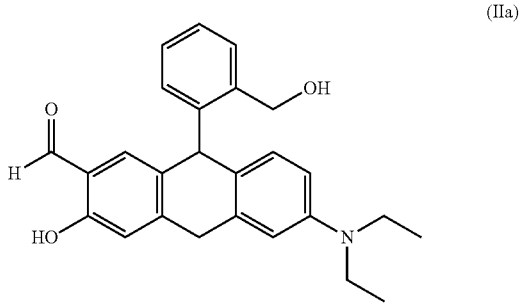

(IIa)

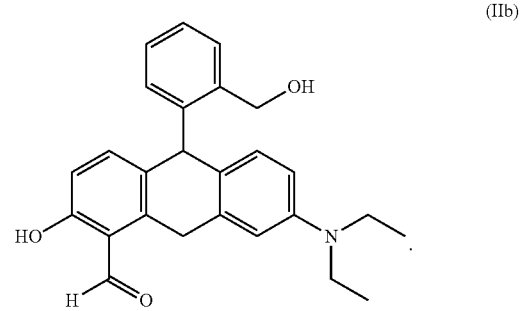

(IIb)

18. A fluorescence imaging probe containing the enzyme-specific retainable fluorescent compound according to claim 7.

19. A composition or kit for visualizing or detecting a target cell in which a specific enzyme is expressed, the composition or kit containing the enzyme-specific retainable fluorescent compound according to claim 7.

20. A method for detecting a target cell in which a specific enzyme is expressed, the method comprising the steps of:
bringing the enzyme-specific retainable fluorescent compound of claim 7 into contact ex vivo with the enzyme expressed in the target cell, and
inducing fluorescence by excitation light irradiation.

* * * * *